US009220776B2

(12) United States Patent
Sharma et al.

(10) Patent No.: US 9,220,776 B2
(45) Date of Patent: Dec. 29, 2015

(54) STABLE FORMULATIONS OF ANTIBODIES TO HUMAN PROGRAMMED DEATH RECEPTOR PD-1 AND RELATED TREATMENTS

(75) Inventors: Manoj K. Sharma, Keasbey, NJ (US); Chakravarthy Nachu Narasimhan, Scotch Plains, NJ (US); Kevin James Gergich, Philadelphia, PA (US); Soonmo Peter Kang, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 156 days.

(21) Appl. No.: 14/008,604

(22) PCT Filed: Mar. 29, 2012

(86) PCT No.: PCT/US2012/031063
§ 371 (c)(1),
(2), (4) Date: Sep. 30, 2013

(87) PCT Pub. No.: WO2012/135408
PCT Pub. Date: Oct. 4, 2012

(65) Prior Publication Data
US 2014/0234296 A1  Aug. 21, 2014

Related U.S. Application Data

(60) Provisional application No. 61/470,121, filed on Mar. 31, 2011.

(51) Int. Cl.
| | | |
|---|---|---|
| *C07K 16/28* | (2006.01) | |
| *A61K 39/395* | (2006.01) | |
| *A61K 9/19* | (2006.01) | |
| *A61K 9/00* | (2006.01) | |
| *A61K 47/18* | (2006.01) | |
| *A61K 47/26* | (2006.01) | |
| *A61K 39/00* | (2006.01) | |

(52) U.S. Cl.
CPC ......... *A61K 39/39591* (2013.01); *A61K 9/0019* (2013.01); *A61K 9/19* (2013.01); *A61K 47/183* (2013.01); *A61K 47/26* (2013.01); *C07K 16/2818* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 7,563,869 B2 | 7/2009 | Honjo et al. | |
| 7,691,379 B2 | 4/2010 | Allan | |
| 2006/0029599 A1 | 2/2006 | Kaisheva et al. | |
| 2009/0208492 A1* | 8/2009 | O'Connor et al. | 424/133.1 |
| 2009/0217401 A1* | 8/2009 | Korman et al. | 800/18 |
| 2010/0055111 A1 | 3/2010 | Sharma | |
| 2010/0137213 A1* | 6/2010 | Fernandez et al. | 514/12 |
| 2010/0266617 A1 | 10/2010 | Carven et al. | |
| 2010/0286038 A1 | 11/2010 | Antochshuk | |
| 2011/0123550 A1* | 5/2011 | Shibayama et al. | 424/172.1 |
| 2011/0256135 A1* | 10/2011 | Fraunhofer et al. | 424/135.1 |

FOREIGN PATENT DOCUMENTS

| | | |
|---|---|---|
| WO | WO9704801 A1 | 2/1997 |
| WO | WO2004056875 A1 | 7/2004 |
| WO | WO2006121168 A1 | 11/2006 |
| WO | WO2008156712 | 12/2008 |
| WO | WO2008157409 | 12/2008 |
| WO | WO2010069858 A1 | 6/2010 |
| WO | WO2011012637 A4 | 2/2011 |

OTHER PUBLICATIONS

Sharpe, A.H, Wherry, E.J., Ahmed R., and Freeman G.J. The function of programmed cell death 1 and its ligands in regulating autoimmunity and infection. Nature Immunology (2007); 8:239-245.

Greenwald R.J., Freeman G.J., and Sharpe A.H. The B7 family revisited. Annual Reviews of Immunology (2005); 23:515-548.

Okazaki T and Honjo T. PD-1 and PD-1 ligands: from discovery to clinical application. International immunology (2007);19:813-824.

Chemnitz et al. SHP-1 and SHP-2 associate with immunoreceptor tyrosine-based switch motif of programmed death 1 upon primary human T cell stimulation, but only receptor ligation prevents activation. J. Immunol. (2004): 173: 945-954.

Nishimura, H., Nose, M., Hiai, H. et al. Development of lupus-like autoimmune diseases by disruption of the PD-1 gene encoding an ITIM motif-carrying immunoreceptor. Immunity (1999);11:141-151.

Okazaki T et al. Autoantibodies against cardiac troponin I are responsible for dilated cardiomyopathy in PD-1 deficient mice. Nature Medicine (2003): 9: 1477-1483.

Ansari MJ. The programmed death-1 pathway regulates diabetes in nonobese diabetic (NOD) mice. J Exp. Med. (2003), Jul. 7;198(1):63-9.

Riley J and Jun. C. The road to recovery: translating PD-1 biology into clinical benefit. Trends in Immunology (2006): 28:48-50.

Barber DL. Restoring function in exhausted CD8 T cells during chronic viral infection. Nature (2006):439: 682-687.

Trautmann L et al. Upregulation of PD-1 expression on HIV-specific CD8+ T cells leads to reversible immune dysfunction. Nature Medicine (2006) 12: 1198-1202.

(Continued)

*Primary Examiner* — Ilia Ouspenski

(57) ABSTRACT

The present invention relates to stable formulations of antibodies against human programmed death receptor PD-1, or antigen binding fragments thereof. The present invention further provides methods for treating various cancers and chronic infections with stable formulations of antibodies against human programmed death receptor PD-1, or antigen binding fragments thereof.

13 Claims, 18 Drawing Sheets

(56) References Cited

OTHER PUBLICATIONS

Petrovas C et al. PD-1 is a regulator of virus-specific CD8+ T cell survival in HIV infection. J Exp. Med. (2006): 203: 2281-2292.

Day CL et al. PD-1 expression on HIV-specific T cells is associated with T-cell exhaustion and disease progression, Nature. Sep. 21, 2006;443(7109):350-4.

Velu V et al. 2009. Enhancing SIV-specific immunity in vivo by PD-1 blockade. Nature (2009) 458: 206-210.

Finnefrock et al. PD-1 blockade in rhesus macaques: inpact on chronic infection and prophylactic vaccination. J. of Immunol. (2009): 182: 980-987.

Dong H et al. Tumor-associated B7-H1 promotes T-cell apoptosis: a potential mechanism of immune evasion. Nat Med. Aug. 2002;8(8):793-800.

Yang et al. PD-1 interaction contributes to the functional suppression of T-cell responses to human uveal melanoma cells in vitro. Invest Ophthalmol Vis Sci. Jun. 2008;49(6 (2008): 49: 2518-2525.

Ghebeh et al. The B7-H1 (PD-L1) T lymphocyte-inhibitory molecule is expressed in breast cancer patients with infiltrating ductal carcinoma: correlation with important high-risk propgnostic factors. Neoplasia (2006) 8: 190-198.

Hamanishi J et al. Programmed cell death 1 ligand 1 and tumor-infiltrating CD8+ T lymphocytes are prognostic factors of human ovarian cancer. Proceeding of the National Academy of Sciences (2007): 104: 3360-3365.

Thompson RH et al. Significance of B7-H1 overexpression in kidney cancer. Clinical Genitourin Cancer (2006): 5: 206-211.

Nomi, T. Sho, M., Akahori, T., et al. Clinical significance and therapeutic potential of the programmed death-1 ligand/programmed death-1 pathway in human pancreatic cancer. Clinical Cancer Research (2007);13:2151-2157.

Ohigashi Y et al. Clinical significance of programmed death-1 ligand-1 and programmed death-1 ligand 2 expression in human esophageal cancer. Clin. Cancer Research (2005): 11: 2947-2953.

Inman et al. PD-L1 (B7-H1) expression by urothelial carcinoma of the bladder and BCG-induced granulomata: associations with localized stage progression. Cancer (2007): 109: 1499-1505.

Shimauchi T et al. Augmented expression of programmed death-1 in both neoplasmatic and nonneoplastic CD4+ T-cells in adult T-cell Leukemia/ Lymphoma. Int. J. Cancer (2007): 121:2585-2590.

Gao et al. Overexpression of PD-L1 significantly associates with tumor aggressiveness and postoperative recurrence in human hepatocellular carcinoma. Clinical Cancer Research (2009) 15: 971-979.

Nakanishi J. Overexpression of B7-H1 (PD-L1) significantly associates with tumor grade and postoperative prognosis in human urothelial cancers. Cancer Immunol Immunother. (2007) 56: 1173-1182.

Hino et al. Tumor cell expression of programmed cell death-1 is a prognostic factor for malignant melanoma. Cancer (2010): 1757-1766.

Daugherty, Ann L., et al.; "Formulation and delivery issues for monoclonal antibody therapeutics"; Advanced Drug Delivery Reviews; 2006; 686-706; 58.

Wang, Wei; "Instability, stabilization, and formulation of liquid protein pharmaceuticals"; International Journal of Pharmaceutics; 1999; 129-188; 185.

Wang, Wei, et al.; "Antibody Structure, Instability, and Formulation"; Journal of Pharmaceutical Sciences; 2007; 1-26; 96(1).

International Search Report, International Application No. PCT/US12/31063, Date of Mailing Jun. 22, 2012.

Written Opinion, International Application No. PCT/US12/31063, Date of Mailing Jun. 22, 2012.

\* cited by examiner

| Stability Data for h409A11 Anti-PD-1 Powder for injection, 50 mg/Vial | | | | | | | | | | |
|---|---|---|---|---|---|---|---|---|---|---|
| Storage Condition | | 5°C | | | | | | | | |
| Batch Number | | 1 | | | | | | | | |
| | | Stability Test Interval | | | | | | | | |
| Test | Clinical Acceptance Criteria | Initial | 1-month | 3-month | 6-month | 9-month | 12-month | 18-month | 24-month |
| Description Lyophilized Powder | White to off-white powder | White cake | White cake | White cake | White cake | White cake | White cake | White cake | White cake |
| Reconstitution Time (seconds) | Report Results | 39 | 36 | 35 | 42 | 43 | 34 | 28 | 45 |
| Description Reconstituted Solution | | | | | | | | | |
| Clarity | Clear to opalescent solution: May contain particulates | Opalescent solution | Opalescent solution | Opalescent solution | Opalescent solution | Opalescent solution | Opalescent solution | Opalescent solution | Opalescent solution |
| Color | Report results by "Y" ref solution | Colorless # | Colorless # | Colorless # | Colorless # | Colorless # | Colorless # | Colorless # | Colorless # |
| pH | 5.0 – 6.0 | 5.6 | 5.5 | 5.5 | 5.6 | 5.6 | 5.6 | 5.6 | 5.6 |
| Assay UV $A_{280}$ nm | 21.3 – 28.8 mg/mL | 24.9 | 24.8 | 24.1 | 24.8 | 24.4 | 25.5 | 24.6 | 23.6 |
| Biological Potency Anti-PD-1 Competitive ELISA (% Relative to control) | 50-150% of Reference | 95 | 80 | 86 | 116 | 93 | 87 | 76 | 83 |
| Purity | | | | | | | | | |
| HPSEC | | | | | | | | | |
| High Molecular Weight Species (%) | ≤ 5.00 | ND | ND | <QL | <QL | <QL | <QL | <QL | <QL |
| Late Eluting Peaks (%) | Report Results | ND | ND | ND | ND | ND | ND | ND | ND |
| Monomer (%) | ≥ 90.0 | 100.0 | 100.0 | 99.8 | 99.8 | 99.8 | 99.8 | 100.0 | 99.8 |
| CE-SDS Reducing | | | | | | | | | |
| % Impurity | ≤ 10.00% species other than heavy and light chains | 0.38 | 0.35 | 0.39 | 0.41 | 0.40 | 0.44 | 0.38 | 0.39 |

FIG.1A

| Stability Data for h409A11 Anti-PD-1 Powder for injection, 50 mg/Vial | | | | | | | | | |
|---|---|---|---|---|---|---|---|---|---|
| Storage Condition | 5°C | | | | | | | | |
| Batch Number | 1 | | | | | | | | |
| | | Stability Test Interval | | | | | | | |
| Test | Clinical Acceptance Criteria | Initial | 1-month | 3-month | 6-month | 9-month | 12-month | 18-month | 24-month |
| CE-SDS Non-Reducing | | | | | | | | | |
| % Impurity | ≤ 10.00% species other than main band | 0.59 | 0.57 | 0.53 | 0.56 | 1.12 | 0.94 | 0.70 | 1.22 |
| HP-IEX | | | | | | | | | |
| Acidic variants (%) | Report Results | 2.5 | 2.5 | 3.3 | 3.2 | 3.3 | 3.4 | 3.2 | 3.3 |
| Acidic 1 (%) | Report Results | 3.7 | 3.7 | 3.6 | 3.9 | 3.9 | 3.9 | 3.7 | 3.8 |
| Acidic 2 (%) | Report Results | 8.2 | 8.5 | 7.7 | 8.0 | 8.1 | 8.3 | 7.8 | 8.0 |
| Main (%) | Report Results | 50.8 | 54.0 | 49.6 | 47.7 | 47.1 | 48.1 | 45.6 | 47.3 |
| Basic 1 (%) | Report Results | 11.0 | 10.6 | 10.7 | 11.3 | 11.7 | 10.4 | 11.5 | 11.0 |
| Basic 2 (%) | Report Results | 8.9 | 8.4 | 8.9 | 8.9 | 9.3 | 9.0 | 9.7 | 8.6 |
| Basic Variants (%) | Report Results | 14.9 | 12.4 | 16.1 | 17.0 | 16.5 | 16.8 | 18.5 | 17.9 |
| Moisture (%) | ≤ 5.0% | 0.3 | 0.4 | 0.3 | 0.5 | 0.4 | 0.4 | 0.7 | 0.6 |
| Particulate Matter (HIAC*) | Complies USP<788> | | | | | | | | |
| ≥ 10 µm per container | NMT 6000 | 51 | 50 | 51 | 50 | 51 | 57 | 43 | 44 |
| ≥ 25 µm per container | NMT 600 | 2 | 3 | 2 | 0 | 4 | 1 | 1 | 0 |
| Bacterial Endotoxin | ≤ 0.25 EU/mg | NT | NT | NT | NT | NT | NT | NT | NT |
| Sterility | Meets Sterility Test Requirement | NT | NT | NT | NT | NT | NT | NT | NT |
| Container Closure Integrity | No leakage detected | NT | NT | NT | NT | NT | NT | NT | NT |

Quantization limit (QL) = 0.25%, Detection Limit (DL) = 0.10%, NT = not tested, ND = not detected
not tested according to "Y" ref solution
* A modified version of USP<788> was used for pre-clinical batch 1

| Stability Data for h409A11 Anti-PD-1 Powder for injection, 50 mg/Vial | | | | | | | |
|---|---|---|---|---|---|---|---|
| Storage Condition | | 25H (25°C, 60% RH) | | | | | |
| Batch Number | | 1 | | | | | |
| | | Stability Test Interval | | | | | |
| Test | Clinical Acceptance Criteria | Initial | 1-month | 3-month | 6-month | 12-month | |
| Description Lyophilized Powder | White to off-white powder | White cake | White cake | White cake | White cake | White cake | |
| Reconstitution Time (seconds) | Report Results | 39 | 39 | 37 | 36 | 32 | |
| Description Reconstituted Solution | | | | | | | |
| Clarity | Clear to opalescent solution: May contain particulates | Opalescent solution | Opalescent solution | Opalescent solution | Opalescent solution | Opalescent solution | |
| Color | Report results by "Y" ref solution | Colorless# | Colorless# | Colorless# | Colorless# | Colorless# | |
| pH | 5.0 – 6.0 | 5.6 | 5.6 | 5.5 | 5.6 | 5.6 | |
| Assay UV $A_{280}$ nm | 21.3 – 28.8 mg/mL | 24.9 | 25.1 | 23.5 | 24.2 | 24.8 | |
| Biological Potency Anti-PD-1 Competitive ELISA (% Relative to control) | 50–150% of Reference | 95 | 80 | 81 | 105 | 96 | |
| Purity | | | | | | | |
| HPSEC | | | | | | | |
| High Mol. Wt. Species (%) | ≤ 5.00 | ND | ND | <QL | <QL | <QL | |
| Late Eluting Peaks (%) | Report Results | ND | ND | ND | ND | ND | |
| Monomer (%) | ≥ 90.0 | 100.0 | 100.0 | 99.8 | 99.8 | 99.8 | |
| CE-SDS Reducing | | | | | | | |
| % Impurity | ≤ 10.00% species other than heavy and light chains | 0.38 | 0.38 | 0.39 | 0.41 | 0.33 | |
| CE-SDS Non-Reducing | | | | | | | |
| % Impurity | ≤ 10.00% species other than main band | 0.59 | 0.57 | 0.71 | 0.58 | 0.98 | |

| Stability Data for h409A11 Anti-PD-1 Powder for injection, 50 mg/Vial | | | | | | |
|---|---|---|---|---|---|---|
| Storage Condition | 25H (25°C, 60% RH) | | | | | |
| Batch Number | | | | | | |
| Test | Clinical Acceptance Criteria | Stability Test Interval | | | | |
| | | Initial | 1-month | 3-month | 6-month | 12-month |
| HP-IEX | | | | | | |
| Acidic variants (%) | Report Results | 2.5 | 2.8 | 3.1 | 3.2 | 3.4 |
| Acidic 1 (%) | Report Results | 3.7 | 3.5 | 3.7 | 4.0 | 4.0 |
| Acidic 2 (%) | Report Results | 8.2 | 8.6 | 8.3 | 8.4 | 9.1 |
| Main (%) | Report Results | 50.8 | 53.4 | 48.6 | 46.7 | 46.6 |
| Basic 1 (%) | Report Results | 11.0 | 10.8 | 10.8 | 11.3 | 10.4 |
| Basic 2 (%) | Report Results | 8.9 | 8.4 | 9.0 | 8.9 | 9.1 |
| Basic Variants (%) | Report Results | 14.9 | 12.6 | 16.5 | 17.5 | 17.4 |
| Moisture (%) | ≤ 5.0% | 0.3 | 0.5 | 0.6 | 0.8 | 0.9 |
| Particulate Matter (HIAC*) | Complies USP<788> | | | | | |
| ≥ 10 μm per container | NMT 6000 | 51 | 31 | 37 | 31 | 59 |
| ≥ 25 μm per container | NMT 600 | 2 | 1 | 1 | 1 | 0 |
| Bacterial Endotoxin | ≤ 0.25 EU/mg | NT | NT | NT | NT | NT |
| Sterility | Meets Sterility Test Requirement | NT | NT | NT | NT | NT |
| Container Closure Integrity | No leakage detected | NT | NT | NT | NT | NT |

Quantization limit (QL) = 0.25%, Detection Limit (DL) = 0.10%, NT = not tested, ND = not detected
not tested according to "Y" ref solution
* A modified version of USP<788> was used for pre-clinical batch 1

| Stability Data for h409A11 Anti-PD-1 Powder for injection, 50 mg/Vial | | | | | | | |
|---|---|---|---|---|---|---|---|
| Storage Condition | | RH4 (40°C, 75% RH) | | | | | |
| Batch Number | | 1 | | | | | |
| | | Stability Test Interval | | | | | |
| Test | Clinical Acceptance Criteria | Initial | 0.5-month | 1-month | 2-month | 3-month | 6-month |
| Description Lyophilized Powder | White to off-white powder | White cake | White cake | White cake | White cake | White cake | White cake |
| Reconstitution Time (seconds) | Report Results | 39 | 31 | 33 | 37 | 33 | 39 |
| Description Reconstituted Solution | | | | | | | |
| Clarity | Clear to opalescent solution; May contain particulates | Opalescent solution | Opalescent solution | Opalescent solution | Opalescent solution | Opalescent solution | Opalescent solution |
| Color | Report results by "Y" ref solution | Colorless# | Colorless# | Colorless# | Colorless# | Colorless# | Colorless# |
| pH | 5.0 – 6.0 | 5.6 | 5.5 | 5.6 | 5.6 | 5.5 | 5.6 |
| Assay UV A280 nm | 21.3 – 28.8 mg/mL | 24.9 | 25.5 | 24.2 | 24.1 | 23.9 | 24.3 |
| Biological Potency Anti-PD-1 Competitive ELISA (% Relative to control) | 50-150% of Reference | 95 | 85 | 83 | 77 | 86 | 97 |
| Purity | | | | | | | |
| HPSEC | | | | | | | |
| High Mol. Wt. Species (%) | ≤ 5.00 | ND | ND | <QL | <QL | 0.27 | 0.30 |
| Late Eluting Peaks (%) | Report Results | ND | ND | ND | ND | ND | ND |
| Monomer (%) | ≥ 90.0 | 100.0 | 100.0 | 99.9 | 99.8 | 99.7 | 99.7 |
| CE-SDS Reducing | | | | | | | |
| % Impurity | ≤ 10.00% species other than heavy and light chains | 0.38 | 0.38 | 0.33 | 0.39 | 0.42 | 0.40 |
| CE-SDS Non-Reducing | | | | | | | |
| % Impurity | ≤ 10.00% species other than main band | 0.59 | 0.58 | 0.56 | 0.50 | 0.60 | 0.72 |

Stability Data for h409A11 Anti-PD-1 Powder for injection, 50 mg/Vial

| Storage Condition | | RH4 (40°C, 75% RH) | | | | | |
|---|---|---|---|---|---|---|---|
| Batch Number | | 1 | | | | | |
| | | Stability Test Interval | | | | | |
| Test | Clinical Acceptance Criteria | Initial | 0.5-month | 1-month | 2-month | 3-month | 6-month |
| HP-IEX | | | | | | | |
| Acidic variants (%) | Report Results | 2.5 | 2.7 | 2.4 | 2.5 | 3.0 | 3.3 |
| Acidic 1 (%) | Report Results | 3.7 | 3.6 | 4.0 | 3.9 | 3.8 | 4.0 |
| Acidic 2 (%) | Report Results | 8.2 | 8.7 | 9.2 | 9.4 | 9.5 | 10.0 |
| Main (%) | Report Results | 50.8 | 50.2 | 52.3 | 50.4 | 46.0 | 43.4 |
| Basic 1 (%) | Report Results | 11.0 | 11.0 | 10.8 | 10.8 | 10.7 | 11.8 |
| Basic 2 (%) | Report Results | 8.9 | 8.8 | 8.4 | 8.7 | 8.7 | 8.8 |
| Basic Variants (%) | Report Results | 14.9 | 15.0 | 12.9 | 14.4 | 18.2 | 18.7 |
| Moisture (%) | ≤ 5.0% | 0.3 | 0.6 | 0.6 | 0.7 | 0.9 | 1.1 |
| Particulate Matter (HIAC*) | Complies USP<788> | | | | | | |
| ≥ 10 μm per container | NMT 6000 | 51 | 40 | 37 | 65 | 28 | 43 |
| ≥ 25 μm per container | NMT 600 | 2 | 3 | 2 | 2 | 1 | 1 |
| Bacterial Endotoxin | ≤ 0.25 EU/mg | NT | NT | NT | NT | NT | NT |
| Sterility | Meets Sterility Test Requirement | NT | NT | NT | NT | NT | NT |
| Container Closure Integrity | No leakage detected | NT | NT | NT | NT | NT | NT |

Quantization limit (QL) = 0.25%, Detection Limit (DL) = 0.10%, NT = not tested, ND = not detected
not tested according to "Y" ref solution
* A modified version of USP<788> was used for pre-clinical batch 1

FIG.3B

| Stability Data for h409A11 Anti-PD-1 Powder for injection, 50 mg/Vial | | | | | | | | | | |
|---|---|---|---|---|---|---|---|---|---|---|
| Storage Condition | | 5°C | | | | | | | | |
| Batch Number | | 2 | | | | | | | | |
| | | Stability Test Interval | | | | | | | | |
| Test | Clinical Acceptance Criteria | Initial | 1-month | 3-month | 6-month | 9-month | 12-month | 18-month | 24-month |
| Description Lyophilized Powder | White to off-white powder | White cake | White cake | White cake | White cake | White cake | White cake | White cake | White cake |
| Reconstitution Time (seconds) | Report Results | 49 | 30 | 36 | 27 | 22 | 23 | 27 | 36 |
| Description Reconstituted Solution | | | | | | | | | |
| Clarity | Clear to opalescent solution: May contain particulates | Opalescent solution | Opalescent solution | Opalescent solution | Opalescent solution | Opalescent solution | Opalescent solution | Opalescent solution | Opalescent solution |
| Color | Report results by "Y" ref solution | Colorless # | Colorless # | Colorless # | Colorless # | Colorless # | Colorless # | Colorless # | Colorless # |
| pH | 5.0 – 6.0 | 5.6 | 5.6 | 5.6 | 5.6 | 5.6 | 5.6 | 5.6 | 5.5 |
| Assay UV $A_{280}$ nm | 21.3 – 28.8 mg/mL | 25.6 | 26.4 | 25.2 | 26.1 | 23.2 | 24.6 | 24.7 | 25.5 |
| Biological Potency Anti-PD-1 Competitive ELISA (% Relative to control) | 50-150% of Reference | 108 | 88 | 86 | 94 | 86 | 82 | 90 | 103 |
| Purity | | | | | | | | | |
| HPSEC | | | | | | | | | |
| High Molecular Weight Species (%) | ≤ 5.00 | 0.52 | 0.30 | 0.31 | 0.31 | 0.32 | <QL | <QL | 0.40 |
| Late Eluting Peaks (%) | Report Results | ND | ND | ND | ND | ND | ND | ND | ND |
| Monomer (%) | ≥ 90.0 | 99.5 | 99.7 | 99.7 | 99.7 | 99.7 | 99.9 | 99.8 | 99.6 |
| CE-SDS Reducing | | | | | | | | | |
| % Impurity | ≤ 10.00% species other than heavy and light chains | 0.37 | 0.36 | 0.38 | 0.37 | 0.38 | 0.39 | 0.45 | 0.64 |

FIG.4A

| Stability Data for h409A11 Anti-PD-1 Powder for injection, 50 mg/Vial | | | | | | | | | |
|---|---|---|---|---|---|---|---|---|---|
| Storage Condition | 5°C | | | | | | | | |
| Batch Number | 2 | | | | | | | | |
| | | Stability Test Interval | | | | | | | |
| Test | Clinical Acceptance Criteria | Initial | 1-month | 3-month | 6-month | 9-month | 12-month | 18-month | 24-month |
| CE-SDS Non-Reducing | | | | | | | | | |
| % Impurity | ≤ 10.00% species other than main band | 0.42 | 0.38 | 0.77 | 0.90 | 0.94 | 0.73 | 1.25 | 1.39 |
| HP-IEX | | | | | | | | | |
| Acidic variants (%) | Report Results | 3.1 | 3.4 | 3.3 | 3.4 | 3.4 | 3.2 | 3.3 | 4.2 |
| Acidic 1 (%) | Report Results | 4.0 | 3.9 | 4.0 | 4.0 | 4.0 | 3.8 | 3.8 | 3.9 |
| Acidic 2 (%) | Report Results | 8.0 | 8.1 | 8.0 | 8.4 | 8.3 | 7.8 | 8.0 | 8.1 |
| Main (%) | Report Results | 47.4 | 47.8 | 47.4 | 47.9 | 47.3 | 45.8 | 47.6 | 46.1 |
| Basic 1 (%) | Report Results | 11.4 | 11.4 | 11.6 | 10.5 | 12.3 | 11.6 | 10.9 | 11.2 |
| Basic 2 (%) | Report Results | 8.8 | 8.9 | 9.2 | 8.9 | 9.4 | 9.6 | 8.5 | 8.7 |
| Basic Variants (%) | Report Results | 17.3 | 16.5 | 16.4 | 16.8 | 15.4 | 18.2 | 17.8 | 17.9 |
| Moisture (%) | ≤ 5.00% | 0.8 | 0.8 | 0.8 | 1.1 | 1.3 | 1.1 | 1.1 | 1.3 |
| Particulate Matter (HIAC*) | Complies USP<788> | | | | | | | | |
| ≥ 10 μm per container | NMT 6000 | 55 | 6 | 35 | 17 | 23 | 1 | 46 | 20 |
| ≥ 25 μm per container | NMT 600 | 0 | 0 | 1 | 1 | 1 | 0 | 0 | 2 |
| Bacterial Endotoxin | ≤ 0.25 EU/mg | NT | NT | NT | NT | NT | NT | NT | NT |
| Sterility | Meets Sterility Test Requirement | NT | NT | NT | NT | NT | NT | NT | NT |
| Container Closure Integrity | No leakage detected | NT | NT | NT | NT | NT | NT | NT | NT |

NT = not tested, ND = not detected,
not tested according to "Y" ref solution
* A modified version of USP<788> was used for pre-clinical batch 2

FIG.4B

| Stability Data for h409A11 Anti-PD-1 Powder for injection, 50 mg/Vial | | | | | |
|---|---|---|---|---|---|
| Storage Condition | | 25H (25°C, 60% RH) | | | |
| Batch Number | | B | | | |
| | | Stability Test Interval | | | |
| Test | Clinical Acceptance Criteria | Initial | 1-month | 3-month | 6-month |
| Description Lyophilized Powder | White to off-white powder | White powder | White powder | White powder | White powder |
| Reconstitution Time (seconds) | Report Results | 49 | 33 | 31 | 23 |
| Description Reconstituted Solution | | | | | |
| Clarity | Clear to opalescent solution: May contain particulates | Opalescent solution | Opalescent solution | Opalescent solution | Opalescent solution |
| Color | Report results by "Y" ref solution | Colorless.# | Colorless.# | Colorless.# | Colorless.# |
| pH | 5.0 – 6.0 | 5.6 | 5.6 | 5.6 | 5.6 |
| Assay UV A280 nm | 21.3 – 28.8 mg/mL | 25.6 | 25.8 | 24.8 | 26.4 |
| Biological Potency Anti-PD-1 Competitive ELISA (%Relative to control) | 50–150% of Reference | 108 | 76 | 78 | 89 |
| Purity | | | | | |
| HPSEC | | | | | |
| High Mol. Wt. Species (%) | ≤ 5.00 | 0.52 | 0.30 | 0.34 | 0.33 |
| Late Eluting Peaks (%) | Report Results | ND | ND | ND | ND |
| Monomer (%) | ≥ 90.0 | 99.5 | 99.7 | 99.7 | 99.7 |
| CE-SDS Reducing | | | | | |
| % Impurity | ≤ 10.00% species other than heavy and light chains | 0.37 | 0.31 | 0.39 | 0.27 |
| CE-SDS Non-Reducing | | | | | |
| % Impurity | ≤ 10.00% species other than main band | 0.42 | 0.44 | 1.10 | 0.96 |

FIG. 5A

| Stability Data for h409A11 Anti-PD-1 Powder for injection, 50 mg/Vial | | | | | |
|---|---|---|---|---|---|
| Storage Condition | | 25H (25°C, 60% RH) | | | |
| Batch Number | | B | | | |
| | | Stability Test Interval | | | |
| Test | Clinical Acceptance Criteria | Initial | 1-month | 3-month | 6-month |
| HP-IEX | | | | | |
| Acidic variants (%) | Report Results | 3.1 | 3.3 | 3.3 | 3.4 |
| Acidic 1 (%) | Report Results | 4.0 | 4.0 | 4.0 | 4.0 |
| Acidic 2 (%) | Report Results | 8.0 | 8.2 | 8.4 | 8.9 |
| Main (%) | Report Results | 47.4 | 47.5 | 47.1 | 47.2 |
| Basic 1 (%) | Report Results | 11.4 | 11.4 | 11.5 | 10.5 |
| Basic 2 (%) | Report Results | 8.8 | 9.0 | 9.1 | 8.8 |
| Basic Variants (%) | Report Results | 17.3 | 16.6 | 16.5 | 17.2 |
| Moisture (%) | ≤ 5.0% | 0.8 | 0.9 | 1.1 | 1.2 |
| Particulate Matter (HIAC*) | Complies USP<788> | | | | |
| ≥ 10 μm per container | NMT 6000 | 55 | 11 | 34 | 6 |
| ≥ 25 μm per container | NMT 600 | 0 | 0 | 1 | 0 |
| Bacterial Endotoxin | ≤ 0.25 EU/mg | NT | NT | NT | NT |
| Sterility | Meets Sterility Test Requirement | NT | NT | NT | NT |
| Container Closure Integrity | No leakage detected | NT | NT | NT | NT |

NT = Not tested, ND = Not detected
not tested according to "Y" ref solution
* A modified version of USP<788> was used for pre-clinical batch 2

FIG.5B

| Stability Data for h409A11 Anti-PD-1 Powder for injection, 50 mg/Vial | | | | | |
|---|---|---|---|---|---|
| Storage Condition | RH4 (40°C, 75% RH) | | | | |
| Batch Number | 2 | | | | |
| | | Stability Test Interval | | | |
| Test | Clinical Acceptance Criteria | Initial | 1-month | 3-month | 6-month |
| Description Lyophilized Powder | White to off-white powder | White powder | White powder | White powder | White powder |
| Reconstitution Time (seconds) | Report Results | 49 | 32 | 35 | 20 |
| Description Reconstituted Solution | | | | | |
| Clarity | Clear to opalescent solution: May contain particulates | Opalescent solution | Opalescent solution | Opalescent solution | Opalescent solution |
| Color | Report results by "Y" ref solution | Colorless# | Colorless# | Colorless# | Colorless# |
| pH | 5.0 – 6.0 | 5.6 | 5.6 | 5.6 | 5.6 |
| Assay UV $A_{280}$ nm | 21.3 – 28.8 mg/mL | 25.6 | 24.9 | 24.9 | 25.9 |
| Biological Potency Anti-PD-1 Competitive ELISA (% Relative to control) | 50-150% of Reference | 108 | 76 | 60 | 66 |
| Purity | | | | | |
| HPSEC | | | | | |
| High Mol. Wt. Species (%) | ≤ 5.00 | 0.52 | 0.34 | 0.37 | 0.38 |
| Late Eluting Peaks (%) | Report Results | ND | ND | ND | ND |
| Monomer (%) | ≥ 90.0 | 99.5 | 99.7 | 99.6 | 99.6 |
| CE-SDS Reducing | | | | | |
| % Impurity | ≤ 10.00% species other than heavy and light chains | 0.37 | 0.39 | 0.45 | 0.34 |
| CE-SDS Non-Reducing | | | | | |
| % Impurity | ≤ 10.00% species other than main band | 0.42 | 0.43 | 1.16 | 0.97 |

FIG. 6A

Stability Data for h409A11 Anti-PD-1 Powder for injection, 50 mg/Vial

| Storage Condition | RH4 (40°C, 75% RH) | | | | |
|---|---|---|---|---|---|
| Batch Number | 3 | | | | |
| | | Stability Test Interval | | | |
| Test | Clinical Acceptance Criteria | Initial | 1-month | 3-month | 6-month |
| HP-IEX | | | | | |
| Acidic variants (%) | Report Results | 3.1 | 3.4 | 3.3 | 3.5 |
| Acidic 1 (%) | Report Results | 4.0 | 4.0 | 4.3 | 4.1 |
| Acidic 2 (%) | Report Results | 8.0 | 8.8 | 9.4 | 10.2 |
| Main (%) | Report Results | 47.4 | 46.8 | 45.9 | 44.8 |
| Basic 1 (%) | Report Results | 11.4 | 11.7 | 11.4 | 10.4 |
| Basic 2 (%) | Report Results | 8.8 | 9.1 | 8.9 | 8.9 |
| Basic Variants (%) | Report Results | 17.3 | 16.4 | 16.8 | 18.0 |
| Moisture (%) | ≤ 5.0% | 0.8 | 1.1 | 1.3 | 1.7 |
| Particulate Matter (HIAC*) | Complies USP<788> | | | | |
| ≥ 10 μm per container | NMT 6000 | 55 | 11 | 14 | 35 |
| ≥ 25 μm per container | NMT 600 | 0 | 0 | 0 | 1 |
| Bacterial Endotoxin | ≤ 0.25 EU/mg | NT | NT | NT | NT |
| Sterility | Meets Sterility Test Requirement | NT | NT | NT | NT |
| Container Closure Integrity | No leakage detected | NT | NT | NT | NT |

NT = not tested, ND = not detected
not tested according to "Y" ref solution
* A modified version of USP<788> was used for pre-clinical batch 2

FIG.6B

| Stability Data for h409A11 Anti-PD-1 Powder for injection, 50 mg/Vial | | | | | | | | | | |
|---|---|---|---|---|---|---|---|---|---|---|
| Storage Condition | | 5°C | | | | | | | | |
| Batch Number | | 3 | | | | | | | | |
| | | Stability Test Interval | | | | | | | | |
| Test | Clinical Acceptance Criteria | Initial | 1-month | 3-month | 6-month | 9-month | 12-month | 18-month | 24-month |
| Description Lyophilized Powder | White to off-white powder | White powder | White powder | White powder | White powder | White powder | White powder | Off-white powder | White powder |
| Reconstitution Time (seconds) | Report Results | 41 | 35 | 34 | 32 | 32 | 38 | 42 | 32 |
| Description Reconstituted Solution | | | | | | | | | |
| Clarity | Clear to opalescent solution: May contain particulates | Opalescent solution does not contain particulates | Clear solution does not contain particulates | Clear solution does not contain particulates | Opalescent solution does not contain particulates | Opalescent solution does not contain particulates | Opalescent solution does not contain particulates | Opalescent solution does not contain particulates | Opalescent solution does not contain particulates |
| Color | Report results by "Y" ref solution | Equivalent to ref solution Y7 | Equivalent to ref solution Y7 | Equivalent to ref solution Y7 | Equivalent to ref solution Y7 | Equivalent to ref solution Y7 | Equivalent to ref solution Y7 | Equivalent to ref solution Y7 | Equivalent to ref solution Y7 |
| pH | 5.0 – 6.0 | 5.5 | 5.5 | 5.5 | 5.5 | 5.5 | 5.5 | 5.5 | 5.5 |
| Assay UV $A_{280}$ nm | 21.3 – 28.8 mg/mL | 25.6 | 25.3 | 25.5 | 25.5 | 25.5 | 26.3 | 26.6 | 25.7 |
| Biological Potency | 50–150% of Reference | 90 | 102 | 96 | 102 | 106 | 105 | 71 | 98 |
| Purity | | | | | | | | | |
| HPSEC | | | | | | | | | |
| High Molecular Weight Species (%) | ≤ 5.00 | 0.32 | 0.27 | 0.28 | 0.25 | 0.31 | 0.36 | 0.32 | 0.36 |
| Late Eluting Peaks (%) | Report Results | <0.13 | <0.13 | <0.13 | <0.13 | <0.13 | <0.13 | <0.13 | <0.13 |
| Monomer (%) | ≥ 90.0 | 99.7 | 99.7 | 99.7 | 99.8 | 99.7 | 99.6 | 99.7 | 99.6 |
| CE-SDS Reducing | | | | | | | | | |
| % Impurity | ≤ 10.00% species other than heavy and light chains | 0.42 | 0.42 | 0.46 | 0.44 | 0.41 | 0.56 | 0.44 | 0.44 |

FIG. 7A

| Stability Data for h409A11 Anti-PD-1 Powder for injection, 50 mg/Vial | | | | | | | | | | |
|---|---|---|---|---|---|---|---|---|---|---|
| Storage Condition | | 5°C | | | | | | | | |
| Batch Number | | 3 | | | | | | | | |
| | | Stability Test Interval | | | | | | | | |
| Test | Clinical Acceptance Criteria | Initial | 1-month | 3-month | 6-month | 9-month | 12-month | 18-month | 24-month |
| CE-SDS Non-Reducing | light chains | | | | | | | | |
| % Impurity | ≤ 10.00% species other than main band | 0.45 | 0.47 | 0.42 | 0.55 | 0.78 | 0.31 | 0.60 | 0.55 |
| HP-IEX | | | | | | | | | |
| Acidic variants (%) | Report Results | 3.97 | 8.45 | 8.06 | 6.79 | 8.52 | 9.29 | 8.71 | 9.70 |
| Acidic 1 (%) | Report Results | 5.45 | 4.99 | 5.05 | 4.97 | 4.75 | 5.07 | 4.90 | 4.91 |
| Acidic 2 (%) | Report Results | 7.76 | 8.26 | 8.26 | 8.02 | 7.91 | 8.48 | 8.48 | 8.59 |
| Main (%) | Report Results | 54.4 | 48.3 | 47.3 | 48.9 | 46.2 | 47.0 | 46.6 | 44.9 |
| Basic 1 (%) | Report Results | 7.23 | 7.63 | 7.82 | 7.98 | 7.69 | 7.77 | 8.04 | 8.43 |
| Basic 2 (%) | Report Results | 7.92 | 8.65 | 9.23 | 9.33 | 9.07 | 8.87 | 9.08 | 9.08 |
| Basic Variants (%) | Report Results | 13.22 | 13.75 | 14.29 | 14.03 | 15.82 | 13.51 | 14.20 | 14.38 |
| Moisture (%) | ≤ 5.0% | 0.8 | 0.8 | 0.9 | 0.8 | 0.8 | 1.0 | 1.0 | 1.0 |
| Particulate Matter (HIAC*) | Complies USP<788> | Complies | Complies | Complies | Complies | Complies | Complies | Complies | Complies |
| ≥ 10 μm per container | NMT 6000 | 39 | 24 | 16 | 18 | 18 | 16 | 16 | 47 |
| ≥ 25 μm per container | NMT 600 | 0 | 1 | 0 | 1 | 0 | 0 | 0 | 2 |
| Bacterial Endotoxin | ≤ 0.25 EU/mg | <0.05 | NT | NT | NT | NT | <0.05 | NT | <0.05 |
| Sterility | Meets Sterility Test Requirement | Meets Requirements | NT | NT | NT | NT | NT | NT | NT |
| Container Closure Integrity | No leakage detected | No leakage detected | NT | NT | NT | NT | No leakage detected | NT | No leakage detected |

NT: Not tested

FIG. 7B

Stability Data for h409A11 Anti-PD-1 Powder for injection, 50 mg/Vial

| Storage Condition | | 25H (25°C, 60% RH) | | | |
|---|---|---|---|---|---|
| Batch Number | | 3 | | | |
| | | Stability Test Interval | | | |
| Test | Clinical Acceptance Criteria | Initial | 1-month | 3-month | 6-month |
| Description Lyophilized Powder | White to off-white powder | White powder | White powder | White powder | White powder |
| Reconstitution Time (seconds) | Report Results | 41 | 35 | 33 | 35 |
| Description Reconstituted Solution | | | | | |
| Clarity | Clear to opalescent solution: May contain particulates | Opalescent solution does not contain particulates | Clear solution does not contain particulates | Clear solution does not contain particulates | Opalescent solution does not contain particulates |
| Color | Report results by "Y" ref solution | Equivalent to ref solution Y7 | Equivalent to ref solution Y7 | Equivalent to ref solution Y7 | Equivalent to ref solution Y7 |
| pH | 5.0 – 6.0 | 5.5 | 5.5 | 5.5 | 5.5 |
| Assay UV A$_{280}$ nm | 21.3 – 28.8 mg/mL | 25.6 | 25.4 | 25.8 | 25.9 |
| Biological Potency | 50–150% of Reference | 90 | 107 | 89 | 99 |
| Purity HPSEC | | | | | |
| High Mol. Wt. Species (%) | ≤ 5.00 | 0.32 | 0.28 | 0.25 | 0.32 |
| Late Eluting Peaks (%) | Report Results | <0.13 | <0.13 | <0.13 | <0.13 |
| Monomer (%) | ≥ 90.0 | 99.7 | 99.7 | 99.7 | 99.7 |
| CE-SDS Reducing | | | | | |
| % Impurity | ≤ 10.00% species other than heavy and light chains | 0.42 | 0.42 | 0.43 | 0.45 |
| CE-SDS Non-Reducing | | | | | |
| % Impurity | ≤ 10.00% species other than main band | 0.45 | 0.71 | 0.43 | 0.53 |

FIG. 8A

| Stability Data for h 409 All Anti-PD-1 Powder for injection, 50 mg/Vial | | | | | |
|---|---|---|---|---|---|
| Storage Condition | 25H (25°C, 60% RH) | | | | |
| Batch Number | 3 | | | | |
| | | Stability Test Interval | | | |
| Test | Clinical Acceptance Criteria | Initial | 1-month | 3-month | 6-month |
| HP-IEX | | | | | |
| Acidic variants (%) | Report Results | 3.97 | 8.52 | 8.67 | 9.79 |
| Acidic 1 (%) | Report Results | 5.45 | 4.97 | 5.09 | 5.04 |
| Acidic 2 (%) | Report Results | 7.76 | 8.40 | 8.60 | 8.49 |
| Main (%) | Report Results | 54.4 | 48.0 | 45.9 | 44.9 |
| Basic 1 (%) | Report Results | 7.23 | 7.65 | 7.89 | 8.09 |
| Basic 2 (%) | Report Results | 7.92 | 8.60 | 9.22 | 9.37 |
| Basic Variants (%) | Report Results | 13.22 | 13.88 | 14.67 | 14.35 |
| Moisture (%) | ≤ 5.0% | 0.8 | 0.9 | 1.0 | 1.2 |
| Particulate Matter (HIAC) | Complies USP<788> | Complies | Complies | Complies | Complies |
| ≥ 10 μm per container | NMT 6000 | 39 | 10 | 18 | 21 |
| ≥ 25 μm per container | NMT 600 | 0 | 0 | 0 | 0 |
| Bacterial Endotoxin | ≤ 0.25 EU/mg | <0.05 | NT | NT | NT |
| Sterility | Meets Sterility Test Requirement | Meets requirements | NT | NT | NT |
| Container Closure Integrity | No leakage detected | No leakage detected | NT | NT | NT |
| NT: Not tested | | | | | |

FIG.8B

| Stability Data for h409A11 Anti-PD-1 Powder for injection, 50 mg/Vial | | | | | |
|---|---|---|---|---|---|
| Storage Condition | | RH4 (40°C, 75% RH) | | | |
| Batch Number | | 3 | | | |
| | | Stability Test Interval | | | |
| Test | Clinical Acceptance Criteria | Initial | 1-month | 3-month | 6-month |
| Description Lyophilized Powder | White to off-white powder | White powder | White powder | White powder | White powder |
| Reconstitution Time (seconds) | Report Results | 41 | 35 | 34 | 33 |
| Description Reconstituted Solution | | | | | |
| Clarity | Clear to opalescent solution: May contain particulates | Opalescent solution does not contain particulates | Clear solution does not contain particulates | Clear solution does not contain particulates | Opalescent solution does not contain particulates |
| Color | Report results by "Y" ref solution | Equivalent to ref solution Y7 | Equivalent to ref solution Y7 | Equivalent to ref solution Y7 | Equivalent to ref solution Y7 |
| pH | 5.0 – 6.0 | 5.5 | 5.5 | 5.5 | 5.5 |
| Assay UV $A_{280}$ nm | 21.3 – 28.8 mg/mL | 25.6 | 25.4 | 25.5 | 25.9 |
| Biological Potency | 50–150% of Reference | 90 | 101 | 105 | 104 |
| Purity | | | | | |
| HPSEC | | | | | |
| High Mol. Wt. Species (%) | ≤ 5.00 | 0.32 | 0.30 | 0.33 | 0.40 |
| Late Eluting Peaks (%) | Report Results | <0.13 | <0.13 | <0.13 | <0.13 |
| Monomer (%) | ≥ 90.0 | 99.7 | 99.7 | 99.7 | 99.6 |
| CE-SDS Reducing | | | | | |
| % Impurity | ≤ 10.00% species other than heavy and light chains | 0.42 | 0.50 | 0.48 | 0.45 |
| CE-SDS Non-Reducing | | | | | |
| % Impurity | ≤ 10.00% species other than main band | 0.45 | 0.52 | 0.67 | 0.35 |

FIG. 9A

| Stability Data for h409A11 Anti-PD-1 Powder for injection, 50 mg/Vial | | | | | |
|---|---|---|---|---|---|
| Storage Condition | RH4 (40°C, 75% RH) | | | | |
| Batch Number | 3 | | | | |
| | | Stability Test Interval | | | |
| Test | Clinical Acceptance Criteria | Initial | 1-month | 3-month | 6-month |
| HP-IEX | | | | | |
| Acidic variants (%) | Report Results | 3.97 | 8.16 | 9.32 | 9.47 |
| Acidic 1 (%) | Report Results | 5.45 | 5.11 | 5.12 | 5.08 |
| Acidic 2 (%) | Report Results | 7.76 | 8.88 | 9.47 | 10.11 |
| Main (%) | Report Results | 54.4 | 47.1 | 43.4 | 42.2 |
| Basic 1 (%) | Report Results | 7.23 | 7.75 | 8.22 | 8.41 |
| Basic 2 (%) | Report Results | 7.92 | 8.51 | 9.11 | 9.12 |
| Basic Variants (%) | Report Results | 13.22 | 14.48 | 15.32 | 15.66 |
| Moisture (%) | ≤ 5.0% | 0.8 | 1.1 | 1.3 | 1.5 |
| Particulate Matter (HIAC) | Complies USP<788> | Complies | Complies | Complies | Complies |
| ≥ 10 μm per container | NMT 6000 | 39 | 14 | 19 | 26 |
| ≥ 25 μm per container | NMT 600 | 0 | 0 | 0 | 1 |
| Bacterial Endotoxin | ≤ 0.25 EU/mg | <0.05 | NT | NT | NT |
| Sterility | Meets Sterility Test Requirement | Meets requirements | NT | NT | NT |
| Container Closure Integrity | No leakage detected | No leakage detected | NT | NT | NT |

NT: Not tested

FIG.9B

SEQUENCE LISTING

```
<160> NUMBER OF SEQ ID NOS: 38

<210> SEQ ID NO 1
<211> LENGTH: 435
<212> TYPE: DNA
<213> ORGANISM: Artificial Sequence
<220> FEATURE:
<223> OTHER INFORMATION: hPD-1.08A heavy chain variable region

<400> SEQUENCE: 1
atgrgatgga gctgtatcat kctcttttg gtagcaacag ctacaggtgt ccactcccag      60
gtccaactgc agcagcctgg ggctgaactg gtgaagcctg gggcttcagt gaagttgtcc    120
tgcaaggcct ctggctacac cttcaccagt tattatctgt actggatgaa acagaggcct    180
ggacaaggcc ttgagtggat tgggggggtt aatcctagta atggtggtac taacttcagt    240
gagaagttca agagcaaggc cacactgact gtagacaaat cctccagcac agcctacatg    300
caactcagca gcctgacatc tgaggactct gcggtctatt actgtacaag aagggattct    360
```

```
aactacgacg ggggctttga ctactggggc caaggcacta ctctcacagt ctcctcagcc    420
aaaacgacac cccca                                                     435

<210> SEQ ID NO 2
<211> LENGTH: 453
<212> TYPE: DNA
<213> ORGANISM: Artificial Sequence
<220> FEATURE:
<223> OTHER INFORMATION: hPD-1.08A light chain variable region

<400> SEQUENCE: 2
atggagacag acacactcct gctatgggta ctgctgctct ggttccagg ttccactggt      60 gacattgtgc tgacacagtc tcctacttcc ttagctgtat ctctggggca gagggccacc   120
atctcatgca gggccagcaa aagtgtcagt acatctggct ttagttattt gcactggtac   180
caacagaaac caggacagcc acccaaactc ctcatctttc ttgcatccaa cctagagtct   240
ggggtccctg ccaggttcag tggcagtggg tctgggacag acttcaccct caacatccat   300
cctgtggagg aggaggacgc tgcaacctat tattgtcagc acagttggga gcttccgctc   360
acgttcggtg ctgggaccaa gctggagctg aaacgggctg atgctgcacc aactgtatcc   420
atcttcccac catccagtaa gcttgggaag ggc                                 453

<210> SEQ ID NO 3
<211> LENGTH: 464
<212> TYPE: DNA
<213> ORGANISM: Artificial Sequence
<220> FEATURE:
<223> OTHER INFORMATION: hPD-1.09A heavy chain variable region

<400> SEQUENCE: 3
atgraatgca gctgggttat yctcttttg gtagcaacag ctacaggtgt ccactcccag      60
gtccaactgc agcagcctgg ggctgaactg gtgaagcctg ggacttcagt gaagttgtcc   120
tgcaaggctt ctggctacac cttcaccaac tactatatgt actgggtgaa gcagaggcct   180
ggacaaggcc ttgagtggat tgggggggatt aatcctagca atggtggtac taacttcaat   240
gagaagttca gaacaaggc cacactgact gtagacagtt cctccagcac aacctacatg    300
caactcagca gcctgacatc tgaggactct gcggtctatt actgtacaag aagggattat   360
aggttcgaca tgggctttga ctactggggc caaggcacca ctctcacagt ctcctcagcc   420
aaaacgacac cccatccgt ytatcccbtg gcccctggaa gctt                     464

<210> SEQ ID NO 4
<211> LENGTH: 438
<212> TYPE: DNA
<213> ORGANISM: Artificial Sequence
<220> FEATURE:
<223> OTHER INFORMATION: hPD-1.09A light chain variable region

<400> SEQUENCE: 4
atggagwcag acacactsct gytatgggta ctgctgctct gggttccagg ttccactggc    60
gacattgtgc tgacacagtc tcctgcttcc ttagctgtat ctctgggaca gagggccgcc   120
atctcatgca gggccagcaa aggtgtcagt acatctggct atagttattt gcactggtac   180
caacagaaac caggacagtc acccaaactc ctcatctatc ttgcatccta cctagaatct   240
ggggtccctg ccaggttcag tggcagtggg tctgggacag acttcaccct caacatccat   300
cctgtggagg aggaggatgc tgcaacctat tactgtcagc acagtaggga ccttccgctc   360
```
acgttcggta ctgggaccaa gctggagctg aaacgggctg atgctgcacc aactgtatcc    420
atcttcccac catccagt                                                   438

<210> SEQ ID NO 5
<211> LENGTH: 122
<212> TYPE: PRT
<213> ORGANISM: Artificial Sequence
<220> FEATURE:
<223> OTHER INFORMATION: hPD-1.08A heavy chain variable region

<400> SEQUENCE: 5

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Leu Tyr Trp Met Lys Gln Arg Pro Gly Gln Gly Leu Glu Trp Ile
        35                  40                  45

Gly Gly Val Asn Pro Ser Asn Gly Gly Thr Asn Phe Ser Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Leu Thr Val Ser Ser Ala Lys
        115                 120

<210> SEQ ID NO 6
<211> LENGTH: 111
<212> TYPE: PRT
<213> ORGANISM: Artificial Sequence
<220> FEATURE:
<223> OTHER INFORMATION: hPD-1.08A light chain variable region

<400> SEQUENCE: 6

Asp Ile Val Leu Thr Gln Ser Pro Thr Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Phe Ser Tyr Leu His Trp Tyr Gln Gln Lys Pro Gly Gln Pro Pro
        35                  40                  45

Lys Leu Leu Ile Phe Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Trp
                85                  90                  95

Glu Leu Pro Leu Thr Phe Gly Ala Gly Thr Lys Leu Glu Leu Lys
            100                 105                 110

<210> SEQ ID NO 7
<211> LENGTH: 122
<212> TYPE: PRT
<213> ORGANISM: Artificial Sequence
<220> FEATURE:
<223> OTHER INFORMATION: hPD-1.09A heavy chain variable region

<400> SEQUENCE: 7

```
Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Thr Phe Thr Asn Tyr
            20                  25                  30

Tyr Met Tyr Trp Val Lys Gln Arg Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Asn Lys Ala Thr Leu Thr Val Asp Ser Ser Ser Thr Thr Tyr
65                  70                  75                  80

Met Gln Leu Ser Ser Leu Thr Ser Glu Asp Ser Ala Val Tyr Tyr Cys
                85                  90                  95

Thr Arg Arg Asp Tyr Arg Phe Asp Met Gly Phe Asp Tyr Trp Gly Gln
                100                 105                 110

Gly Thr Thr Leu Thr Val Ser Ser Ala Lys
            115                 120
```

<210> SEQ ID NO 8
<211> LENGTH: 111
<212> TYPE: PRT
<213> ORGANISM: Artificial Sequence
<220> FEATURE:
<223> OTHER INFORMATION: hPD-1.09A light chain variable region

<400> SEQUENCE: 8

```
Asp Ile Val Leu Thr Gln Ser Pro Ala Ser Leu Ala Val Ser Leu Gly
1               5                   10                  15

Gln Arg Ala Ala Ile Ser Cys Arg Ala Ser Lys Gly Val Ser Thr Ser
            20                  25                  30

Gly Tyr Ser Tyr Leu His Trp Tyr Gln Gln Lys Pro Gly Gln Ser Pro
        35                  40                  45

Lys Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Asp Leu Pro Leu Thr Phe Gly Thr Gly Thr Lys Leu Glu Leu Lys
                100                 105                 110
```

<210> SEQ ID NO 9
<211> LENGTH: 15
<212> TYPE: PRT
<213> ORGANISM: Artificial Sequence
<220> FEATURE:
<223> OTHER INFORMATION: hPD-1.08A light chain CDR1

<400> SEQUENCE: 9

```
Arg Ala Ser Lys Ser Val Ser Thr Ser Gly Phe Ser Tyr Leu His
1               5                   10                  15
```

<210> SEQ ID NO 10
<211> LENGTH: 7
<212> TYPE: PRT
<213> ORGANISM: Artificial Sequence
<220> FEATURE:
<223> OTHER INFORMATION: hPD-1.08A light chain CDR2

<400> SEQUENCE: 10

```
Leu Ala Ser Asn Leu Glu Ser
```

```
<210> SEQ ID NO 11
<211> LENGTH: 9
<212> TYPE: PRT
<213> ORGANISM: Artificial Sequence
<220> FEATURE:
<223> OTHER INFORMATION: hPD-1-08A light chain CDR3

<400> SEQUENCE: 11

Gln His Ser Trp Glu Leu Pro Leu Thr
1               5

<210> SEQ ID NO 12
<211> LENGTH: 5
<212> TYPE: PRT
<213> ORGANISM: Artificial Sequence
<220> FEATURE:
<223> OTHER INFORMATION: hPD-1.08A heavy chain CDR1

<400> SEQUENCE: 12

Ser Tyr Tyr Leu Tyr
1               5

<210> SEQ ID NO 13
<211> LENGTH: 17
<212> TYPE: PRT
<213> ORGANISM: Artificial Sequence
<220> FEATURE:
<223> OTHER INFORMATION: hPD-1.08A heavy chain CDR2

<400> SEQUENCE: 13

Gly Val Asn Pro Ser Asn Gly Gly Thr Asn Phe Ser Glu Lys Phe Lys
1               5                   10                  15

Ser

<210> SEQ ID NO 14
<211> LENGTH: 11
<212> TYPE: PRT
<213> ORGANISM: Artificial Sequence
<220> FEATURE:
<223> OTHER INFORMATION: hPD-1.08A heavy chain CDR3

<400> SEQUENCE: 14

Arg Asp Ser Asn Tyr Asp Gly Gly Phe Asp Tyr
1               5                   10

<210> SEQ ID NO 15
<211> LENGTH: 15
<212> TYPE: PRT
<213> ORGANISM: Artificial Sequence
<220> FEATURE:
<223> OTHER INFORMATION: hPD-1.09A light chain CDR1

<400> SEQUENCE: 15

Arg Ala Ser Lys Gly Val Ser Thr Ser Gly Tyr Ser Tyr Leu His
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: hPD-1.09A light chain CDR2

<400> SEQUENCE: 16
```

-continued

Leu Ala Ser Tyr Leu Glu Ser
1               5

<210> SEQ ID NO 17
<211> LENGTH: 9
<212> TYPE: PRT
<213> ORGANISM: Artificial Sequence
<220> FEATURE:
<223> OTHER INFORMATION: hPD-1.09A light chain CDR3

<400> SEQUENCE: 17

Gln His Ser Arg Asp Leu Pro Leu Thr
1               5

<210> SEQ ID NO 18
<211> LENGTH: 5
<212> TYPE: PRT
<213> ORGANISM: Artificial Sequence
<220> FEATURE:
<223> OTHER INFORMATION: hPD-1.09A heavy chain CDR1

<400> SEQUENCE: 18

Asn Tyr Tyr Met Tyr
1               5

<210> SEQ ID NO 19
<211> LENGTH: 17
<212> TYPE: PRT
<213> ORGANISM: Artificial Sequence
<220> FEATURE:
<223> OTHER INFORMATION: hPD-1.09A heavy chain CDR2

<400> SEQUENCE: 19

Gly Ile Asn Pro Ser Asn Gly Gly Thr Asn Phe Asn Glu Lys Phe Lys
1               5                   10                  15

Asn

<210> SEQ ID NO 20
<211> LENGTH: 11
<212> TYPE: PRT
<213> ORGANISM: Artificial Sequence
<220> FEATURE:
<223> OTHER INFORMATION: hPD-1.09A heavy chain CDR3

<400> SEQUENCE: 20

Arg Asp Tyr Arg Phe Asp Met Gly Phe Asp Tyr
1               5                   10

<210> SEQ ID NO 21
<211> LENGTH: 417
<212> TYPE: DNA
<213> ORGANISM: Artificial Sequence
<220> FEATURE:
<223> OTHER INFORMATION: 109A-H heavy chain variable region
<220> FEATURE:
<221> NAME/KEY: sig_peptide
<222> LOCATION: (1)..(57)

<400> SEQUENCE: 21
atggactgga cctggagcat ccttttcttg gtggcagcac caacaggagc ccactcccaa      60
gtgcagctgg tgcagtctgg agttgaagtg aagaagcccg ggcctcagt gaaggtctcc     120 tgcaaggctt ctggctacac ctttaccaac tactatatgt actgggtgcg acaggcccct    180
ggacaagggc ttgagtggat gggagggatt aatcctagca atggtggtac taacttcaat    240
gagaagttca agaacagagt caccttgacc acagactcat ccacgaccac agcctacatg    300

```
gaactgaaga gcctgcaatt tgacgacacg gccgtttatt actgtgcgag aagggattat    360
aggttcgaca tgggctttga ctactggggc caagggacca cggtcaccgt ctcgagc      417
```

<210> SEQ ID NO 22
<211> LENGTH: 417
<212> TYPE: DNA
<213> ORGANISM: Artificial Sequence
<220> FEATURE:
<223> OTHER INFORMATION: Codon optimized 109A-H heavy chain variable
      region
<220> FEATURE:
<221> NAME/KEY: sig_peptide
<222> LOCATION: (1)..(57)

<400> SEQUENCE: 22

```
atggactgga cctggtctat cctgttcctg gtggccgctc ctaccggcgc tcactcccag    60
gtgcagctgg tgcagtccgg cgtggaggtg aagaagcctg gcgcctccgt caaggtgtcc   120
tgcaaggcct ccggctacac cttcaccaac tactacatgt actgggtgcg gcaggctccc   180
ggccagggac tggagtggat gggcggcatc aaccccttcca acggcggcac caacttcaac   240
gagaagttca gaaccgggt gaccctgacc accgactcct ccaccaccac cgcctacatg    300
gagctgaagt ccctgcagtt cgacgacacc gccgtgtact actgcgccag cgggactac    360 cggttcgaca tgggcttcga ctactggggc cagggcacca ccgtgaccgt gtcctcc      417
```

<210> SEQ ID NO 23
<211> LENGTH: 1398
<212> TYPE: DNA
<213> ORGANISM: Artificial Sequence
<220> FEATURE:
<223> OTHER INFORMATION: Codon optimized 409A-H heavy chain full length
<220> FEATURE:
<221> NAME/KEY: sig_peptide
<222> LOCATION: (1)..(57)

<400> SEQUENCE: 23

```
atggccgtgc tgggcctgct gttctgcctg gtgaccttcc cttcctgcgt gctgtcccag    60
gtgcagctgg tgcagtccgg cgtggaggtg aagaagcctg gcgcctccgt caaggtgtcc   120
tgtaaggcct ccggctacac cttcaccaac tactacatgt actgggtgcg gcaggcccca   180
ggccagggac tggagtggat gggcggcatc aaccccttcca acggcggcac caacttcaac   240
gagaagttca gaaccgggt gaccctgacc accgactcct ccaccacaac cgcctacatg    300
gaactgaagt ccctgcagtt cgacgacacc gccgtgtact actgcgccag cgggactac    360 cggttcgaca tgggcttcga ctactggggc cagggcacca ccgtgaccgt gtcctccgct   420
agcaccaagg gcccttccgt gttccctctg gccccttgct ccggtccac ctccgagtcc    480 accgccgctc tgggctgtct ggtgaaggac tacttccctg agcctgtgac cgtgagctgg   540
aactctggcg ccctgacctc cggcgtgcac accttccctg ccgtgctgca gtcctccggc   600
ctgtactccc tgtcctccgt ggtgaccgtg ccttcctcct ccctgggcac caagacctac   660
acctgcaacg tggaccacaa gccttccaac accaaggtgg acaagcgggt ggagtccaag   720 tacgccctc cttgccctcc ctgccctgcc ctgagttcc tgggcggacc ctccgtgttc    780
ctgttccctc ctaagcctaa ggacaccctg atgatctccc ggacccctga ggtgacctgc   840
gtggtggtgg acgtgtccca ggaagatcct gaggtccagt tcaattggta cgtggatggc   900
gtggaggtgc acaacgccaa gaccaagcct cgggaggaac agttcaactc cacctaccgg   960
gtggtgtctg tgctgaccgt gctgcaccag gactggctga acggcaagga atacaagtgc  1020
```

```
aaggtcagca acaagggcct gccctcctcc atcgagaaaa ccatctccaa ggccaagggc    1080
cagcctcgcg agcctcaggt gtacaccctg cctcctagcc aggaagagat gaccaagaat    1140
caggtgtccc tgacatgcct ggtgaagggc ttctaccctt ccgatatcgc cgtggagtgg    1200
gagagcaacg gccagccaga gaacaactac aagaccaccc ctcctgtgct ggactccgac    1260
ggctccttct tcctgtactc caggctgacc gtggacaagt cccggtggca ggaaggcaac    1320
gtcttttcct gctccgtgat gcacgaggcc ctgcacaacc actacaccca gaagtccctg    1380
tccctgtctc tgggcaag                                                  1398

<210> SEQ ID NO 24
<211> LENGTH: 393
<212> TYPE: DNA
<213> ORGANISM: Artificial Sequence
<220> FEATURE:
<223> OTHER INFORMATION: K09A-L-11 light chain variable region
<220> FEATURE:
<221> NAME/KEY: sig_peptide
<222> LOCATION: (1)..(60)

<400> SEQUENCE: 24
atggaagccc cagctcagct tctcttcctc ctgctactct ggctcccaga taccaccgga     60
gaaattgtgt tgacacagtc tccagccacc ctgtctttgt ctccagggga aagagccacc    120
ctctcctgca gggccagcaa aggtgtcagt acatctggct atagttattt gcactggtat    180
caacagaaac ctggccaggc tcccaggctc ctcatctatc ttgcatccta cctagaatct    240
ggcgtcccag ccaggttcag tggtagtggg tctgggacag acttcactct caccatcagc    300
agcctagagc ctgaagattt tgcagtttat tactgtcagc acagcaggga ccttccgctc    360
acgttcggcg agggaccaa agtggagatc aaa                                  393

<210> SEQ ID NO 25
<211> LENGTH: 393
<212> TYPE: DNA
<213> ORGANISM: Artificial Sequence
<220> FEATURE:
<223> OTHER INFORMATION: K09A-L-16 light chain variable region
<220> FEATURE:
<221> NAME/KEY: sig_peptide
<222> LOCATION: (1)..(60)

<400> SEQUENCE: 25
atggaaaccc cagcgcagct tctcttcctc ctgctactct ggctcccaga taccaccgga     60
gaaattgtgc tgactcagtc tccactctcc ctgcccgtca ccctggaga gccggcctcc    120 atctcctgca gggccagcaa aggtgtcagt acatctggct atagttattt gcattggtac    180
ctccagaagc cagggcagtc tccacagctc ctgatctatc ttgcatccta cctagaatct    240
ggggtccctg acaggttcag tggcagtgga tcaggcacag attttacact gaaaatcagc    300
agagtggagg ctgaggatgt tggggtttat tactgccagc atagtaggga ccttccgctc    360
acgtttggcc aggggaccaa gctggagatc aaa                                 393

<210> SEQ ID NO 26
<211> LENGTH: 393
<212> TYPE: DNA
<213> ORGANISM: Artificial Sequence
<220> FEATURE:
<223> OTHER INFORMATION: K09A-L-17 light chain variable region
<220> FEATURE:
<221> NAME/KEY: sig_peptide
<222> LOCATION: (1)..(60)
```

<400> SEQUENCE: 26

```
atgaggctcc ctgctcagct cctggggctg ctaatgctct gggtctctgg atccagtggg      60
gatattgtga tgacccagac tccactctcc ctgcccgtca cccctggaga gccggcctcc     120
atctcctgca gggccagcaa aggtgtcagt acatctggct atagttattt gcattggtat     180
ctgcagaagc cagggcagtc tccacagctc ctgatctatc ttgcatccta cctagaatct     240
ggagtcccag acaggttcag tggcagtggg tcaggcactg ctttcacact gaaaatcagc     300
agggtggagg ctgaggatgt tggactttat tactgccagc atagtaggga ccttccgctc     360
acgtttggcc aggggaccaa gctggagatc aaa                                  393
```

<210> SEQ ID NO 27
<211> LENGTH: 390
<212> TYPE: DNA
<213> ORGANISM: Artificial Sequence
<220> FEATURE:
<223> OTHER INFORMATION: Codon optimized K09A-L-11 light chain variable
    region
<220> FEATURE:
<221> NAME/KEY: sig_peptide
<222> LOCATION: (1)..(57)

<400> SEQUENCE: 27

```
atggcccctg tgcagctgct gggcctgctg gtgctgttcc tgcctgccat gcggtgcgag      60
atcgtgctga cccagtcccc tgccaccctg tccctgagcc ctggcgagcg ggctaccctg     120
agctgcagag cctccaaggg cgtgtccacc tccggctact cctacctgca ctggtatcag     180
cagaagccag gccaggcccc tcggctgctg atctacctgg cctcctacct ggagtccggc     240
gtgcctgccc ggttctccgg ctccggaagc ggcaccgact tcaccctgac catctcctcc     300
ctggagcctg aggacttcgc cgtgtactac tgccagcact cccgggacct gcctctgacc     360
tttggcggcg gaacaaaggt ggagatcaag                                      390
```

<210> SEQ ID NO 28
<211> LENGTH: 390
<212> TYPE: DNA
<213> ORGANISM: Artificial Sequence
<220> FEATURE:
<223> OTHER INFORMATION: Codon optimized K09A-L-16 light chain variable
    region
<220> FEATURE:
<221> NAME/KEY: sig_peptide
<222> LOCATION: (1)..(57)

<400> SEQUENCE: 28

```
atggcccctg tgcagctgct gggcctgctg gtgctgttcc tgcctgccat gcggtgcgag      60
atcgtgctga cccagtcccc tctgtccctg cctgtgaccc ctggcgagcc tgcctccatc     120
tcctgccggg cctccaaggg cgtgtccacc tccggctact cctacctgca ctggtatctg     180
cagaagcctg gccagtcccc ccagctgctg atctacctgg cctcctacct ggagtccggc     240
gtgcctgacc ggttctccgg ctccggcagc ggcaccgact caccctgaa gatctcccgg     300
gtggaggccg aggacgtggg cgtgtactac tgccagcact cccgggacct gcctctgacc     360
ttcggccagg gcaccaagct ggagatcaag                                      390
```

<210> SEQ ID NO 29
<211> LENGTH: 390
<212> TYPE: DNA
<213> ORGANISM: Artificial Sequence
<220> FEATURE:

<223> OTHER INFORMATION: Codon optimized K09A-L-17 light chain variable
      region
<220> FEATURE:
<221> NAME/KEY: sig_peptide
<222> LOCATION: (1)..(57)

<400> SEQUENCE: 29
atggcccctg tgcagctgct gggcctgctg gtgctgttcc tgcctgccat gcggtgcgac     60
atcgtgatga cccagacccc tctgtccctg cctgtgaccc tggcgagcc tgcctccatc    120 tcctgccggg cctccaaggg cgtgtccacc tccggctact cctacctgca ctggtatctg    180
cagaagcctg gccagtcccc tcagctgctg atctacctgg cctcctacct ggagtccggc    240
gtgcctgacc ggttctccgg ctccggaagc ggcaccgctt ttaccctgaa gatctccaga    300
gtggaggccg aggacgtggg cctgtactac tgccagcact cccgggacct gcctctgacc    360
ttcggccagg gcaccaagct ggagatcaag                                     390

<210> SEQ ID NO 30
<211> LENGTH: 139
<212> TYPE: PRT
<213> ORGANISM: Artificial Sequence
<220> FEATURE:
<223> OTHER INFORMATION: 109A-H heavy chain variable region
<220> FEATURE:
<221> NAME/KEY: sig_peptide
<222> LOCATION: (1)..(19)

<400> SEQUENCE: 30

Met Asp Trp Thr Trp Ser Ile Leu Phe Leu Val Ala Ala Pro Thr Gly
1               5                   10                  15

Ala His Ser Gln Val Gln Leu Val Gln Ser Gly Val Glu Val Lys Lys
            20                  25                  30

Pro Gly Ala Ser Val Lys Val Ser Cys Lys Ala Ser Gly Tyr Thr Phe
        35                  40                  45

Thr Asn Tyr Tyr Met Tyr Trp Val Arg Gln Ala Pro Gly Gln Gly Leu
    50                  55                  60

Glu Trp Met Gly Gly Ile Asn Pro Ser Asn Gly Gly Thr Asn Phe Asn
65                  70                  75                  80

Glu Lys Phe Lys Asn Arg Val Thr Leu Thr Thr Asp Ser Ser Thr Thr
                85                  90                  95

Thr Ala Tyr Met Glu Leu Lys Ser Leu Gln Phe Asp Asp Thr Ala Val
            100                 105                 110

Tyr Tyr Cys Ala Arg Arg Asp Tyr Arg Phe Asp Met Gly Phe Asp Tyr
        115                 120                 125

Trp Gly Gln Gly Thr Thr Val Thr Val Ser Ser
    130                 135

<210> SEQ ID NO 31
<211> LENGTH: 466
<212> TYPE: PRT
<213> ORGANISM: Artificial Sequence
<220> FEATURE:
<223> OTHER INFORMATION: 409A-H heavy chain full length
<220> FEATURE:
<221> NAME/KEY: sig_peptide
<222> LOCATION: (1)..(19)

<400> SEQUENCE: 31

Met Ala Val Leu Gly Leu Leu Phe Cys Leu Val Thr Phe Pro Ser Cys
1               5                   10                  15

Val Leu Ser Gln Val Gln Leu Val Gln Ser Gly Val Glu Val Lys Lys

-continued

```
                20                  25                  30
Pro Gly Ala Ser Val Lys Val Ser Cys Lys Ala Ser Gly Tyr Thr Phe
            35                  40                  45
Thr Asn Tyr Tyr Met Tyr Trp Val Arg Gln Ala Pro Gly Gln Gly Leu
        50                  55                  60
Glu Trp Met Gly Gly Ile Asn Pro Ser Asn Gly Thr Asn Phe Asn
65                  70                  75                  80
Glu Lys Phe Lys Asn Arg Val Thr Leu Thr Thr Asp Ser Ser Thr Thr
                85                  90                  95
Thr Ala Tyr Met Glu Leu Lys Ser Leu Gln Phe Asp Asp Thr Ala Val
            100                 105                 110
Tyr Tyr Cys Ala Arg Arg Asp Tyr Arg Phe Asp Met Gly Phe Asp Tyr
            115                 120                 125
Trp Gly Gln Gly Thr Thr Val Thr Val Ser Ser Ala Ser Thr Lys Gly
            130                 135                 140
Pro Ser Val Phe Pro Leu Ala Pro Cys Ser Arg Ser Thr Ser Glu Ser
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
            195                 200                 205
Thr Val Pro Ser Ser Ser Leu Gly Thr Lys Thr Tyr Thr Cys Asn Val
        210                 215                 220
Asp His Lys Pro Ser Asn Thr Lys Val Asp Lys Arg Val Glu Ser Lys
225                 230                 235                 240
Tyr Gly Pro Pro Cys Pro Pro Cys Pro Ala Pro Glu Phe Leu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser Gln Glu
            275                 280                 285
Asp Pro Glu Val Gln Phe Asn Trp Tyr Val Asp Gly Val Glu Val His
290                 295                 300
Asn Ala Lys Thr Lys Pro Arg Glu Glu Gln Phe Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Gly Leu Pro Ser Ser Ile Glu
            340                 345                 350
Lys Thr Ile Ser Lys Ala Lys Gly Gln Pro Arg Glu Pro Gln Val Tyr
            355                 360                 365
Thr Leu Pro Pro Ser Gln Glu Glu Met Thr Lys Asn Gln Val Ser Leu
        370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Arg Leu Thr Val Asp
            420                 425                 430
Lys Ser Arg Trp Gln Glu Gly Asn Val Phe Ser Cys Ser Val Met His
            435                 440                 445
```

Glu Ala Leu His Asn His Tyr Thr Gln Lys Ser Leu Ser Leu Ser Leu
    450                 455                 460

Gly Lys
465

<210> SEQ ID NO 32
<211> LENGTH: 130
<212> TYPE: PRT
<213> ORGANISM: Artificial Sequence
<220> FEATURE:
<223> OTHER INFORMATION: K09A-L-11 light chain variable region
<220> FEATURE:
<221> NAME/KEY: sig_peptide
<222> LOCATION: (1)..(19)

<400> SEQUENCE: 32

Met Ala Pro Val Gln Leu Leu Gly Leu Leu Val Leu Phe Leu Pro Ala
1               5                   10                  15

Met Arg Cys Glu Ile Val Leu Thr Gln Ser Pro Ala Thr Leu Ser Leu
            20                  25                  30

Ser Pro Gly Glu Arg Ala Thr Leu Ser Cys Arg Ala Ser Lys Gly Val
        35                  40                  45

Ser Thr Ser Gly Tyr Ser Tyr Leu His Trp Tyr Gln Gln Lys Pro Gly
    50                  55                  60

Gln Ala Pro Arg Leu Leu Ile Tyr Leu Ala Ser Tyr Leu Glu Ser Gly
65                  70                  75                  80

Val Pro Ala Arg Phe Ser Gly Ser Gly Ser Gly Thr Asp Phe Thr Leu
                85                  90                  95

Thr Ile Ser Ser Leu Glu Pro Glu Asp Phe Ala Val Tyr Tyr Cys Gln
            100                 105                 110

His Ser Arg Asp Leu Pro Leu Thr Phe Gly Gly Gly Thr Lys Val Glu
        115                 120                 125

Ile Lys
    130

<210> SEQ ID NO 33
<211> LENGTH: 130
<212> TYPE: PRT
<213> ORGANISM: Artificial Sequence
<220> FEATURE:
<223> OTHER INFORMATION: K09A-L-16 light chain variable region
<220> FEATURE:
<221> NAME/KEY: sig_peptide
<222> LOCATION: (1)..(19)

<400> SEQUENCE: 33

Met Ala Pro Val Gln Leu Leu Gly Leu Leu Val Leu Phe Leu Pro Ala
1               5                   10                  15

Met Arg Cys Glu Ile Val Leu Thr Gln Ser Pro Leu Ser Leu Pro Val
            20                  25                  30

Thr Pro Gly Glu Pro Ala Ser Ile Ser Cys Arg Ala Ser Lys Gly Val
        35                  40                  45

Ser Thr Ser Gly Tyr Ser Tyr Leu His Trp Tyr Leu Gln Lys Pro Gly
    50                  55                  60

Gln Ser Pro Gln Leu Leu Ile Tyr Leu Ala Ser Tyr Leu Glu Ser Gly
65                  70                  75                  80

Val Pro Asp Arg Phe Ser Gly Ser Gly Ser Gly Thr Asp Phe Thr Leu
                85                  90                  95

Lys Ile Ser Arg Val Glu Ala Glu Asp Val Gly Val Tyr Tyr Cys Gln

His Ser Arg Asp Leu Pro Leu Thr Phe Gly Gln Gly Thr Lys Leu Glu
        115                 120                 125

Ile Lys
    130

<210> SEQ ID NO 34
<211> LENGTH: 130
<212> TYPE: PRT
<213> ORGANISM: Artificial Sequence
<220> FEATURE:
<223> OTHER INFORMATION: K09A-L-17 light chain variable region
<220> FEATURE:
<221> NAME/KEY: sig_peptide
<222> LOCATION: (1)..(19)

<400> SEQUENCE: 34

Met Ala Pro Val Gln Leu Leu Gly Leu Leu Val Leu Phe Leu Pro Ala
1               5                   10                  15

Met Arg Cys Asp Ile Val Met Thr Gln Thr Pro Leu Ser Leu Pro Val
            20                  25                  30

Thr Pro Gly Glu Pro Ala Ser Ile Ser Cys Arg Ala Ser Lys Gly Val
        35                  40                  45

Ser Thr Ser Gly Tyr Ser Tyr Leu His Trp Tyr Leu Gln Lys Pro Gly
    50                  55                  60

Gln Ser Pro Gln Leu Leu Ile Tyr Leu Ala Ser Tyr Leu Glu Ser Gly
65                  70                  75                  80

Val Pro Asp Arg Phe Ser Gly Ser Gly Ser Gly Thr Ala Phe Thr Leu
                85                  90                  95

Lys Ile Ser Arg Val Glu Ala Glu Asp Val Gly Leu Tyr Tyr Cys Gln
            100                 105                 110

His Ser Arg Asp Leu Pro Leu Thr Phe Gly Gln Gly Thr Lys Leu Glu
        115                 120                 125

Ile Lys
    130

<210> SEQ ID NO 35
<211> LENGTH: 469
<212> TYPE: PRT
<213> ORGANISM: Artificial Sequence
<220> FEATURE:
<223> OTHER INFORMATION: 109A-H heavy chain full length
<220> FEATURE:
<221> NAME/KEY: sig_peptide
<222> LOCATION: (1)..(19)

<400> SEQUENCE: 35

Met Ala Val Leu Gly Leu Leu Phe Cys Leu Val Thr Phe Pro Ser Cys
1               5                   10                  15

Val Leu Ser Gln Val Gln Leu Val Gln Ser Gly Val Glu Val Lys Lys
            20                  25                  30

Pro Gly Ala Ser Val Lys Val Ser Cys Lys Ala Ser Gly Tyr Thr Phe
        35                  40                  45

Thr Asn Tyr Tyr Met Tyr Trp Val Arg Gln Ala Pro Gly Gln Gly Leu
    50                  55                  60

Glu Trp Met Gly Gly Ile Asn Pro Ser Asn Gly Gly Thr Asn Phe Asn
65                  70                  75                  80

Glu Lys Phe Lys Asn Arg Val Thr Leu Thr Thr Asp Ser Ser Thr Thr
                85                  90                  95

```
Thr Ala Tyr Met Glu Leu Lys Ser Leu Gln Phe Asp Asp Thr Ala Val
                100                 105                 110
Tyr Tyr Cys Ala Arg Arg Asp Tyr Arg Phe Asp Met Gly Phe Asp Tyr
            115                 120                 125
Trp Gly Gln Gly Thr Thr Val Thr Val Ser Ser Ala Ser Thr Lys Gly
        130                 135                 140
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
        195                 200                 205
Thr Val Pro Ser Ser Leu Gly Thr Gln Thr Tyr Ile Cys Asn Val
210                 215                 220
Asn His Lys Pro Ser Asn Thr Lys Val Asp Lys Lys Val Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
        275                 280                 285
Ser His Glu Asp Pro Glu Val Lys Phe Asn Trp Tyr Val Asp Gly Val
290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Asp Glu Leu Thr Lys Asn Gln
    370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
    450                 455                 460
Leu Ser Pro Gly Lys
465

<210> SEQ ID NO 36
<211> LENGTH: 237
<212> TYPE: PRT
<213> ORGANISM: Artificial Sequence
<220> FEATURE:
<223> OTHER INFORMATION: K09A-L-11 light chain full length
```

-continued

```
<220> FEATURE:
<221> NAME/KEY: sig_peptide
<222> LOCATION: (1)..(19)

<400> SEQUENCE: 36

Met Ala Pro Val Gln Leu Leu Gly Leu Leu Val Leu Phe Leu Pro Ala
1               5                   10                  15

Met Arg Cys Glu Ile Val Leu Thr Gln Ser Pro Ala Thr Leu Ser Leu
                20                  25                  30

Ser Pro Gly Glu Arg Ala Thr Leu Ser Cys Arg Ala Ser Lys Gly Val
            35                  40                  45

Ser Thr Ser Gly Tyr Ser Tyr Leu His Trp Tyr Gln Gln Lys Pro Gly
    50                  55                  60

Gln Ala Pro Arg Leu Leu Ile Tyr Leu Ala Ser Tyr Leu Glu Ser Gly
65                  70                  75                  80

Val Pro Ala Arg Phe Ser Gly Ser Gly Ser Gly Thr Asp Phe Thr Leu
                85                  90                  95

Thr Ile Ser Ser Leu Glu Pro Glu Asp Phe Ala Val Tyr Tyr Cys Gln
                100                 105                 110

His Ser Arg Asp Leu Pro Leu Thr Phe Gly Gly Gly Thr Lys Val Glu
                115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
                180                 185                 190

Asp Ser Thr Tyr Ser Leu Ser Ser Thr Leu Thr Leu Ser Lys Ala Asp
                195                 200                 205

Tyr Glu Lys His Lys Val Tyr Ala Cys Glu Val Thr His Gln Gly Leu
            210                 215                 220

Ser Ser Pro Val Thr Lys Ser Phe Asn Arg Gly Glu Cys
225                 230                 235

<210> SEQ ID NO 37
<211> LENGTH: 237
<212> TYPE: PRT
<213> ORGANISM: Artificial Sequence
<220> FEATURE:
<223> OTHER INFORMATION: K09A-L-16 light chain full length
<220> FEATURE:
<221> NAME/KEY: sig_peptide
<222> LOCATION: (1)..(19)

<400> SEQUENCE: 37

Met Ala Pro Val Gln Leu Leu Gly Leu Leu Val Leu Phe Leu Pro Ala
1               5                   10                  15

Met Arg Cys Glu Ile Val Leu Thr Gln Ser Pro Leu Ser Leu Pro Val
                20                  25                  30

Thr Pro Gly Glu Pro Ala Ser Ile Ser Cys Arg Ala Ser Lys Gly Val
            35                  40                  45

Ser Thr Ser Gly Tyr Ser Tyr Leu His Trp Tyr Leu Gln Lys Pro Gly
    50                  55                  60

Gln Ser Pro Gln Leu Leu Ile Tyr Leu Ala Ser Tyr Leu Glu Ser Gly
65                  70                  75                  80
```

```
Val Pro Asp Arg Phe Ser Gly Ser Gly Ser Gly Thr Asp Phe Thr Leu
             85                  90                  95

Lys Ile Ser Arg Val Glu Ala Glu Asp Val Gly Val Tyr Tyr Cys Gln
            100                 105                 110

His Ser Arg Asp Leu Pro Leu Thr Phe Gly Gln Gly Thr Lys Leu Glu
            115                 120                 125

Ile Lys Arg Thr Val Ala Ala Pro Ser Val Phe Ile Phe Pro Pro Ser
            130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
            210                 215                 220

Ser Ser Pro Val Thr Lys Ser Phe Asn Arg Gly Glu Cys
225                 230                 235
```

<210> SEQ ID NO 38
<211> LENGTH: 237
<212> TYPE: PRT
<213> ORGANISM: Artificial Sequence
<220> FEATURE:
<223> OTHER INFORMATION: K09A-L-17 light chain full length
<220> FEATURE:
<221> NAME/KEY: sig_peptide
<222> LOCATION: (1)..(19)

<400> SEQUENCE: 38

```
Met Ala Pro Val Gln Leu Leu Gly Leu Leu Val Leu Phe Leu Pro Ala
1               5                   10                  15

Met Arg Cys Asp Ile Val Met Thr Gln Thr Pro Leu Ser Leu Pro Val
             20                  25                  30

Thr Pro Gly Glu Pro Ala Ser Ile Ser Cys Arg Ala Ser Lys Gly Val
             35                  40                  45

Ser Thr Ser Gly Tyr Ser Tyr Leu His Trp Tyr Leu Gln Lys Pro Gly
         50                  55                  60

Gln Ser Pro Gln Leu Leu Ile Tyr Leu Ala Ser Tyr Leu Glu Ser Gly
65                  70                  75                  80

Val Pro Asp Arg Phe Ser Gly Ser Gly Ser Gly Thr Ala Phe Thr Leu
             85                  90                  95

Lys Ile Ser Arg Val Glu Ala Glu Asp Val Gly Leu Tyr Tyr Cys Gln
            100                 105                 110

His Ser Arg Asp Leu Pro Leu Thr Phe Gly Gln Gly Thr Lys Leu Glu
            115                 120                 125

Ile Lys Arg Thr Val Ala Ala Pro Ser Val Phe Ile Phe Pro Pro Ser
            130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190
```

```
Asp Ser Thr Tyr Ser Leu Ser Ser Thr Leu Thr Leu Ser Lys Ala Asp
        195                 200                 205
Tyr Glu Lys His Lys Val Tyr Ala Cys Glu Val Thr His Gln Gly Leu
    210                 215                 220
Ser Ser Pro Val Thr Lys Ser Phe Asn Arg Gly Glu Cys
225                 230                 235
```

STABLE FORMULATIONS OF ANTIBODIES TO HUMAN PROGRAMMED DEATH RECEPTOR PD-1 AND RELATED TREATMENTS

CROSS REFERENCE TO RELATED APPLICATIONS

This application claims the benefit of U.S. provisional patent application No. 61/470,121, filed Mar. 31, 2011, which is herein incorporated by reference in its entirety.

FIELD OF THE INVENTION

The present invention relates to stable formulations of antibodies against human programmed death receptor PD-1, or antigen binding fragments thereof. The present invention further provides methods for treating various cancers and chronic infections with stable formulations of antibodies against human PD-1, or antigen binding fragments thereof.

BACKGROUND OF THE INVENTION

Programmed Death 1 (PD-1), a member of the CD28 costimulatory gene family, is moderately expressed on naive T, B and NKT cells and up-regulated by TB cell receptor signaling on lymphocytes, monocytes and myeloid cells (1). PD-1 has two known ligands with distinct expression profiles, PD-L1 (B7-H1) and PD-L2 (B7-DC). PD-L2 expression is relatively restricted and is found on activated dendritic cells, macrophages and monocytes and on vascular endothelial cells (1-3). In contrast, PD-L1 is expressed more broadly including on naive lymphocytes and its expression is induced on activated B and T cells, monocytes and dendritic cells. Furthermore, by mRNA, it is expressed by non-lymphoid tissues including vascular endothelial cells, epithelial cells and muscle cells.

PD-1 is recognized as an important player in immune regulation and the maintenance of peripheral tolerance. In the mouse, this was shown to require PD-L1 expression on peripheral tissues and ligation of PD-1 on potentially autoreactive T cells to negatively modulate T cell activation involving an ITIM sequence in the PD-1 cytoplasmic domain (1, 4).

Depending on the specific genetic background, pdcd1$^{-/-}$ mice spontaneously develop lupus-like phenomena or dilated cadiomyopathy (5, 6). Furthermore, antibody-induced blockade of the PD-1/PD-L 1 pathway was demonstrated to accelerate the onset of autoimmune insulitis and diabetes in NOD mice (7).

Human cancers arising in various tissues were found to over-express PD-L1 or PD-L2. In large sample sets of e.g. ovarian, renal, colorectal, pancreatic, liver cancers and melanoma it was shown that PD-L1 expression correlated with poor prognosis and reduced overall survival irrespective of subsequent treatment (15-26). Similarly, PD-1 expression on tumor infiltrating lymphocytes was found to mark dysfunctional T cells in breast cancer and melanoma (27-28) and to correlate with poor prognosis in renal cancer (29). Using primary patient samples, it was shown that blockade of PD-1 or PD-L1 in vitro results in enhancement of human tumor-specific T cell activation and cytokine production (30). Consequently, in several murine syngeneic tumor models, blockade of either PD-1 or PD-L1 significantly inhibited tumor growth or induced complete regression.

A PD-1 blocking mAb (h409A11) was discovered and developed for use to treat human cancer patients and chronic virus-infected patients (described in co-pending application WO2008/156712).

Antigen-specific T cell dysfunction or tolerance is exemplified by the accumulated loss of the potential to produce Interleukin 2 (IL-2), Tumor Necrosis factor (TNF) α, perforin, interferon (IFN) γ (8) and inability to mount a proliferative response to T cell receptor triggering (1). The PD-1 pathway controls antigen-specific T cell tolerance and was found to be exploited in viral infection and tumor development to control and evade effective T cell immunity.

In chronic infection with LCMV (mouse), HIV, HBV or HCV (human), antigen-specific T cells were found to express aberrantly high levels of PD-1 correlating with their state of anergy or dysfunction (9). Blocking the PD-1-PD-L1 interaction in vivo (LCMV) or in vitro (HIV, HCV, HBV) was shown to revive anti-viral T cell activity (10-12). PD-1 blockade in recently Simian Immunodeficiency Virus-infected macaques resulted in strong reduction of viral load and increased survival (13). Similarly, reduction in viral load was confirmed in second study using long-term SIV-infected rhesus macaques (14).

Overall, the PD-1/PD-L1 pathway is a well-validated target for the development of antibody therapeutics for cancer treatment. Anti-PD-1 antibodies are also useful for treating chronic viral infection. Memory CD8$^+$ T cells generated after an acute viral infection are highly functional and constitute an important component of protective immunity. In contrast, chronic infections are often characterized by varying degrees of functional impairment (exhaustion) of virus-specific T-cell responses, and this defect is a principal reason for the inability of the host to eliminate the persisting pathogen. Although functional effector T cells are initially generated during the early stages of infection, they gradually lose function during the course of a chronic infection. Barber et al. (Barber et al., Nature 439: 682-687 (2006)) showed that mice infected with a laboratory strain of LCMV developed chronic infection resulting in high levels of virus in the blood and other tissues. These mice initially developed a robust T cell response, but eventually succumbed to the infection upon T cell exhaustion. The authors found that the decline in number and function of the effector T cells in chronically infected mice could be reversed by injecting an antibody that blocked the interaction between PD-1 and PD-L1.

PD-1 has also been shown to be highly expressed on T cells from HIV infected individuals and that receptor expression correlates with impaired T cell function and disease progression (Day et al., Nature 443:350-4 (2006); Trautmann L. et al., Nat. Med. 12: 1198-202 (2006)). In both studies, blockade of the PD-1 pathway using antibodies against the ligand PD-L1 significantly increased the expansion of HIV-specific, IFN-gamma producing cells in vitro.

Other studies also implicate the importance of the PD-1 pathway in controlling viral infection. PD-1 knockout mice exhibit better control of adenovirus infection than wild-type mice (Iwai et al., Exp. Med. 198:39-50 (2003)). Also, adoptive transfer of HBV-specific T cells into HBV transgenic animals initiated hepatitis (Isogawa M. et al., Immunity 23:53-63 (2005)). The disease state of these animals oscillates as a consequence of antigen recognition in the liver and PD-1 upregulation by liver cells.

Therapeutic antibodies may be used to block cytokine activity. A significant limitation in using antibodies as a therapeutic agent in vivo is the immunogenicity of the antibodies. As most monoclonal antibodies are derived from non-human species, repeated use in humans results in the generation of an immune response against the therapeutic antibody. Such an immune response results in a loss of therapeutic efficacy at a minimum, and potentially a fatal anaphylactic response. Accordingly, antibodies of reduced immunogenicity in humans, such as humanized or fully human antibodies, are preferred for treatment of human subjects. Exemplary therapeutic antibodies specific for human PD-1 are disclosed in commonly-assigned U.S. Patent Application Publication No. US2010/0266617, and in International Patent Publication No. WO2008/156712, the disclosures of which are hereby incorporated by reference in their entireties.

Antibodies for use in human subjects must be stored prior to use and transported to the point of administration. Reproducibly attaining a desired level of antibody drug in a subject requires that the drug be stored in a formulation that maintains the bioactivity of the drug. The need exists for stable formulations of anti-human PD-1 antibodies for pharmaceutical use, e.g., for treating various cancers and infectious diseases. Preferably, such formulations will exhibit a long shelf-life, be stable when stored and transported, and will be amenable to administration at high concentrations, e.g. for use in subcutaneous administration, as well as low concentrations, e.g. for intravenous administration.

SUMMARY OF THE INVENTION

The present invention relates to stable formulations of antibodies against human programmed death receptor PD-1, or antigen binding fragments thereof. The present invention further provides methods for treating various cancers and chronic infections with stable formulations of antibodies against human programmed death receptor PD-1, or antigen binding fragments thereof.

In certain embodiments, the invention relates to a lyophilized formulation of an anti-human PD-1 antibody, or antigen binding fragment thereof, comprising: a) said anti-human PD-1 antibody, or antigen binding fragment thereof; b) histidine buffer; c) polysorbate 80; and d) sucrose.

In certain embodiments, the formulation has a pH between 5.0 and 6.0 when reconstituted.

In certain embodiments, the lyophilized formulation enables reconstitution of the antibody, or antigen binding fragment thereof, at a concentration of between about 25 mg/mL and 100 mg/mL.

In certain embodiments, polysorbate 80 is present at a weight ratio of approximately 0.02% (w/v).

In certain embodiments, sucrose is present at a weight ratio of approximately 7% (w/v).

In yet additional embodiments, the invention relates to a lyophilized pharmaceutical formulation of an anti-human PD-1 antibody, or antigen binding fragment thereof, made by lyophilizing an aqueous solution comprising: a) 25-100 mg/mL anti-antibody, or antigen binding fragment thereof; b) about 70 mg/mL sucrose; c) about 0.2 mg/mL polysorbate 80; and d) about 10 mM histidine buffer at pH 5.0-6.0.

In certain embodiments, the anti-human PD-1 antibody, or antigen binding fragment thereof, is present at about 25 mg/mL in the aqueous solution. In certain embodiments, the aqueous solution has a pH of about 5.5.

In yet additional embodiments, the invention relates to a lyophilized pharmaceutical formulation of an anti-human PD-1 antibody, or antigen binding fragment thereof; that when reconstituted comprises: a) 25-100 mg/mL anti-human PD-1 antibody, or antigen binding fragment thereof; b) about 70 mg/mL sucrose; c) about 0.2 mg/mL polysorbate 80; and d) about 10 mM Histidine buffer at about pH 5.0-pH 6.0.

In certain embodiments, the anti-human PD-1 antibody, or antigen binding fragment thereof; is present at about 25 mg/mL in the reconstituted solution. In certain embodiments, the reconstituted solution has a pH of about 5.5.

In yet additional embodiments, the invention relates to a liquid pharmaceutical formulation of an anti-human PD-1 antibody, or antigen binding fragment thereof comprising: a) 25-100 mg/mL anti-antibody, or antigen binding fragment thereof; b) about 70 mg/mL sucrose; c) about 0.2 mg/mL polysorbate 80; and d) about 10 mM histidine buffer at pH 5.0-6.0.

In yet additional embodiments, the invention relates to a pharmaceutical formulation of an anti-human PD-1 antibody, or antigen binding fragment thereof comprising: a) said anti-human PD-1 antibody, or antigen binding fragment thereof; b) histidine buffer; c) polysorbate 80; and d) sucrose. In certain embodiments, the formulation has a pH between 5.0 and 6.0 when reconstituted. In certain embodiments, the polysorbate 80 is present at a weight ratio of approximately 0.02% (w/v). In certain embodiments, the sucrose is present at a weight ratio of approximately 7% (w/v).

In yet additional embodiments, the invention relates to any of the formulations described herein, wherein the antibody, or antigen binding fragment thereof; comprises a light chain comprising three CDR sequences selected from the group consisting of SEQ ID NOs: 9, 10, 11, 15, 16, and 17.

In yet additional embodiments, the invention relates to any of the formulations described herein, wherein the antibody, or antigen binding fragment thereof; comprises a heavy chain comprising three CDR sequences selected from the group consisting of SEQ ID NOs: 12, 13, 14, 18, 19, and 20.

In yet additional embodiments, the invention relates to any of the formulations described herein, wherein the antibody, or antigen binding fragment thereof, comprises: i) a light chain comprising three CDR sequences SEQ ID NOs: 15, 16, and 17; and ii) a heavy chain comprising three CDR sequences SEQ ID NOs: 8, 19, and 20.

In yet additional embodiments, the invention relates to any of the formulations described herein, wherein the antibody, or antigen binding fragment thereof, comprises a light chain variable domain comprising amino acid residues 20 to 130 of SEQ ID NO:32.

In yet additional embodiments, the invention relates to any of the formulations described herein, wherein the antibody, or antigen binding fragment thereof, comprises a heavy chain variable domain comprising SEQ ID NO:31.

In yet additional embodiments, the invention relates to any of the formulations described herein, wherein the antibody, or antigen binding fragment thereof, comprises: i) a light chain comprising amino acid residues 20 to 237 of SEQ ID NO: 36 and ii) a heavy chain comprising amino acid residues 20 to 466 of SEQ ID NO: 31.

In yet additional embodiments, the invention relates to any of the formulations described herein, wherein the antibody is selected from the group consisting of h409A11, h409A16, and h409A17.

In yet additional embodiments, the invention relates to a method of treating chronic infection in a mammalian subject in need thereof comprising: administering an effective amount of any of the formulations described herein.

In yet additional embodiments, the invention relates to a method of treating cancer in a mammalian subject in need thereof, the method comprising administering an effective amount of any of the formulations described herein. In certain embodiments, the effective amount comprises a dose of anti-human PD-1 antibody selected from the group consisting of the 1.0, 3.0, and 10 mg/kg.

BRIEF DESCRIPTION OF THE DRAWINGS

FIGS. 1A-B show stability data for lyophilized formulations of h409A11 at pH 5.5 stored at 5° C. (24 months).

FIGS. 2A-B show stability data for lyophilized formulations of h409A11 at pH 5.5 stored at 25H conditions (25° C., 60% RH, 12 months).

FIGS. 3A-B show stability data for lyophilized formulations of h409A11 at pH 5.5 stored at RH4 conditions (40° C., 75% RH, 6 months).

FIGS. 4A-B show stability data for lyophilized formulations of h409A11 stored at 5° C. (24 months).

FIGS. 5A-B show stability data for lyophilized formulations of h409A11 at pH 5.5 stored at 25H conditions (25° C., 60% RH, 6 months).

FIGS. 6A-B show stability data for lyophilized formulations of h409A11 at pH 5.5 stored at RH4 conditions (40° C., 75% RH, 6 months).

FIGS. 7A-B show stability data for lyophilized formulations of h409A11 stored at 5° C. (24 months).

FIGS. 8A-B show stability data for lyophilized formulations of h409A11 25H conditions (25° C., 60% RH, 6 months).

FIGS. 9A-B show stability data for lyophilized formulations of h409A11 at RH4 conditions (40° C., 75% RH, 6 months).

DETAILED DESCRIPTION

The present invention provides formulations of anti-PD-1 antibodies and uses thereof for treating various cancers and infectious diseases.

Anti-PD-1 antibody h409A11 is an exemplary antibody in the stable formulations described herein. Three humanized anti-PD-1 monoclonal antibodies (i.e., h409A11, h409A16, and h509A17) suitable for the present formulations are described in co-pending patent publication WO2008/156712. Additionally, formulations described herein are useful for treating certain cancers as well as chronic infections. Table 2 provides a list of the corresponding CDR sequences for h409A11. Table 6 provides a list of sequences of exemplary anti-PD-1 antibodies.

In accordance with the present invention there may be employed conventional molecular biology, microbiology, protein expression and purification, antibody, and recombinant DNA techniques within the skill of the art. Such techniques are explained fully in the literature. See, e.g., Sambrook et al. (2001) *Molecular Cloning: A Laboratory Manual.* 3rd ed. Cold Spring Harbor Laboratory Press: Cold Spring Harbor, N.Y.; Ausubel et al. eds. (2005) *Current Protocols in Molecular Biology.* John Wiley and Sons, Inc.: Hoboken, N.J.; Bonifacino et al. eds. (2005) *Current Protocols in Cell Biology.* John Wiley and Sons, Inc.: Hoboken, N.J.; Coligan et al. eds. (2005) *Current Protocols in Immunology,* John Wiley and Sons, Inc.: Hoboken, N.J.; Coico et al. eds. (2005) *Current Protocols in Microbiology,* John Wiley and Sons, Inc.: Hoboken, N.J.; Coligan et al. eds. (2005) *Current Protocols in Protein Science,* John Wiley and Sons, Inc.: Hoboken, N.J.; and Enna et al. eds. (2005) *Current Protocols in Pharmacology,* John Wiley and Sons, Inc.: Hoboken, N.J.; *Nucleic Acid Hybridization,* Hames & Higgins eds. (1985); *Transcription And Translation,* Hames & Higgins, eds. (1984); *Animal Cell Culture Freshney,* ed. (1986); *Immobilized Cells And Enzymes,* IRL Press (1986); Perbal, *A Practical Guide To Molecular Cloning* (1984); and Harlow and Lane. *Antibodies: A Laboratory Manual* (Cold Spring Harbor Laboratory Press: 1988).

I. Definitions

As used herein, the term "antibody" refers to any form of antibody that exhibits the desired biological activity. Thus, it is used in the broadest sense and specifically covers monoclonal antibodies (including full length monoclonal antibodies), polyclonal antibodies, multispecific antibodies (e.g., bispecific antibodies), chimeric antibodies, humanized antibodies, fully human antibodies, etc. so long as they exhibit the desired biological activity.

Adjuvant

As used herein, the term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.,* 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, BCG (*bacille Calmette-Guerin*) and *Corynebacterium parvum*. Preferably, the adjuvant is pharmaceutically acceptable.

Cytokine

The term "cytokine" is a generic term for proteins released by one cell population which act on another cell as intercellular mediators. Examples of such cytokines are lymphokines, monokines, chemokines, and traditional polypeptide hormones. Examplary cytokines include: human IL-2, IFN-γ, IL-6, TNFα, IL-17, and IL-5.

Cytotoxic Agent

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$) chemotherapeutic agents, and toxins such as enzymatically active toxins of bacterial, fungal, plant or animal origin, or fragments thereof.

Therapeutic Uses and Methods

The PD-1 blocking agents include those which specifically bind to human PD-1, can be used to increase, enhance, stimulate or up-regulate an immune response. Desirable subjects include human patients in need of enhancement of an immune response including patients with cancer and/or a chronic viral infection.

Cancer

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, hodgkin's lymphoma, non-hodgkin's lymphoma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer.

PD-1 blocking agents include those used to treat cancer (i.e., to inhibit the growth or survival of tumor cells). Preferred cancers whose growth may be inhibited using anti-PD-1 antibodies such as humanized anti-PD-1 antibody h409A11 and include cancers typically responsive to immunotherapy, but also cancers that have not hitherto been associated with immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), pancreatic adenocarcinoma, breast cancer, colon cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. Malignancies that demonstrate improved disease-free and overall survival in relation to the presence of tumor-infiltrating lymphocytes in biopsy or surgical material, e.g. melanoma, colorectal, liver, kidney, stomach/esophageal, breast, pancreas, and ovarian cancer are encompassed in the methods and treatments described herein. Such cancer subtypes are known to be susceptible to immune control by T lymphocytes. Additionally, included are refractory or recurrent malignancies whose growth may be inhibited using the antibodies described herein. Particularly preferred cancers include those characterized by elevated expression of PD-1 and/or its ligands PD-L1 and/or PD-L2 in tested tissue samples, including: ovarian, renal, colorectal, pancreatic, breast, liver, gastric, esophageal cancers and melanoma. Additional cancers that can benefit from treatment with anti-PD-1 antibodies such as humanized anti-PD-1 antibody h409A11 include those associated with persistent infection with viruses such as human immunodeficiency viruses, hepatitis viruses class A, B and C, Epstein Barr virus, human papilloma viruses that are known to be causally related to for instance Kaposi's sarcoma, liver cancer, nasopharyngeal cancer, lymphoma, cervical, vulval, anal, penile and oral cancers.

Chemotherapeutic Agent

A "chemotherapeutic agent" is a chemical compound useful in the treatment of cancer. Anti-PD-1 antibodies can be used with any one or more suitable chemotherapeutic agent. Examples of such chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

Growth Inhibitory Agent

A "growth inhibitory agent" when used herein refers to a compound or composition which inhibits growth of a cell, especially cancer cell over expressing any of the genes identified herein, either in vitro or in vivo. Thus, the growth inhibitory agent is one which significantly reduces the percentage of cells over expressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine) taxanes, and topo II inhibitors such as doxorubicin, epirubicin, daunorubicin, and etoposide. Those agents that arrest G1 also spill over into S-phase arrest, for example, DNA alkylating agents such as dacarbazine, mechlorethamine, and cisplatin. Further information can be found in *The Molecular Basis of Cancer*, Mendelsohn and Israel, eds., Chapter 1, entitled "Cell cycle regulation, oncogens, and antineoplastic drugs" by Murakami et al. (WB Saunders: Philadelphia, 1995).

Antibody or Antibody Fragments in Combination with Additional Agents

Anti-PD-1 antibody or antibody fragments can be used alone or in combination with: other anti-neoplastic agents or immunogenic agents (for example, attenuated cancerous cells, tumor antigens (including recombinant proteins, peptides, and carbohydrate molecules), antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF); standard cancer treatments (for example, chemotherapy, radiotherapy or surgery); or other antibodies (including but not limited to antibodies to VEGF, EGFR, Her2/neu, VEGF receptors, other growth factor receptors, CD20, CD40, CD-40L, CTLA-4, OX-40, 4-1BB, and ICOS).

Infectious Diseases

Antagonist anti-PD-1 antibodies or antibody fragments can also be used to prevent or treat infections and infectious disease. These agents can be used alone, or in combination with vaccines, to stimulate the immune response to pathogens, toxins, and self-antigens. The antibodies or antigen-binding fragment thereof can be used to stimulate immune response to viruses infectious to humans, including but not limited to: human immunodeficiency viruses, hepatitis viruses class A, B and C, Epstein Barr virus, human cytomegalovirus, human papilloma viruses, and herpes viruses. Antagonist anti-PD-1 antibodies or antibody fragments can be used to stimulate immune response to infection with bacterial or fungal parasites, and other pathogens. Viral infections with hepatitis B and C and HIV are among those considered to be chronic viral infections.

As used herein, the terms "PD-1 binding fragment," "antigen binding fragment thereof," "binding fragment thereof" or "fragment thereof" encompass a fragment or a derivative of an antibody that still substantially retains its biological activity of binding to antigen (human PD-1) and inhibiting its activity (e.g., blocking the binding of PD-1 to PDL1 and PDL2). Therefore, the term "antibody fragment" or PD-1 binding fragment refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; and multispecific antibodies formed from antibody fragments. Typically, a binding fragment or derivative retains at least 10% of its PD-1 inhibitory activity. Preferably, a binding fragment or derivative retains at least 25%, 50%, 60%, 70%, 80%, 90%, 95%, 99% or 100% (or more) of its PD-1 inhibitory activity, although any binding fragment with sufficient affinity to exert the desired biological effect will be useful. It is also intended that a PD-1 binding fragment can include variants having conservative amino acid substitutions that do not substantially alter its biologic activity.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) *Nature* 305: 537-39. Alternatively, bispecific antibodies can be prepared using chemical linkage. See, e.g., Brennan et al. (1985) *Science* 229:81. Bispecific antibodies include bispecific antibody fragments. See, e.g., Holliger et al. (1993) *Proc. Natl. Acad. Sci. U.S.A.* 90:6444-48, Gruber et al. (1994) *J. Immunol.* 152:5368.

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079). Single domain antibodies comprising two $V_H$ domains with modifications such that single domain antibodies are formed are also included.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The humanized forms of rodent antibodies will generally comprise the same CDR sequences of the parental rodent antibodies, although certain amino acid substitutions may be included to increase affinity, increase stability of the humanized antibody, or for other reasons.

The antibodies of the present invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) *J. Allergy Clin. Immunol.* 116:731 at 734-35.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody which comprises mouse immunoglobulin sequences only. A fully human antibody may be generated in a human being, in a transgenic animal having human immunoglobulin germline sequences, by phage display or other molecular biological methods.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain (Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain (Chothia and Lesk (1987) *J. Mol. Biol.* 196: 901-917). As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing.

"Conservatively modified variants" or "conservative substitution" refers to substitutions of amino acids are known to those of skill in this art and may be made generally without altering the biological activity of the resulting molecule, even in essential regions of the polypeptide. Such exemplary substitutions are preferably made in accordance with those set forth in Table 1 as follows:

TABLE 1

Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |
| Cys (C) | Ser; Ala |

TABLE 1-continued

Exemplary Conservative Amino Acid Substitutions

| Original residue | Conservative substitution |
|---|---|
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

In addition, those of skill in this art recognize that, in general, single amino acid substitutions in non-essential regions of a polypeptide do not substantially alter biological activity. See, e.g., Watson et al. (1987) *Molecular Biology of the Gene*, The Benjamin/Cummings Pub. Co., p. 224 (4th Edition).

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a binding compound that consists essentially of a recited amino acid sequence may also include one or more amino acids, including substitutions of one or more amino acid residues, that do not materially affect the properties of the binding compound.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

The antibody, or binding composition derived from the antigen-binding site of an antibody, of the contemplated formulation or method binds to its antigen with an affinity that is at least two fold greater, preferably at least ten times greater, more preferably at least 20-times greater, and most preferably at least 100-times greater than the affinity with unrelated antigens. In a preferred embodiment the antibody will have an affinity that is greater than about $10^9$ liters/mol, as determined, e.g., by Scatchard analysis. Munsen et al. (1980) *Analyt. Biochem.* 107:220-239.

Pharmaceutical Composition Definitions

The term "bulking agents" comprise agents that provide the structure of the freeze-dried product. Common examples used for bulking agents include mannitol, glycine, lactose and sucrose. In addition to providing a pharmaceutically elegant cake, bulking agents may also impart useful qualities in regard to modifying the collapse temperature, providing freeze-thaw protection, and enhancing the protein stability over long-term storage. These agents can also serve as tonicity modifiers.

The term "buffer" encompasses those agents which maintain the solution pH in an acceptable range prior to lyophilization and may include succinate (sodium or potassium), histidine, phosphate (sodium or potassium), Tris (tris (hydroxymethyl)aminomethane), diethanolamine, citrate (sodium) and the like. The buffer of this invention has a pH in the range from about 5.0 to about 6.0; and preferably has a pH of about 5.5. Examples of buffers that will control the pH in this range include succinate (such as sodium succinate), gluconate, histidine, citrate and other organic acid buffers. In arriving at the exemplary formulation, histidine, acetate and citrate buffers in the pH range of 5.0-6.0 were explored for suitability. Histine and acetate buffer systems performed better than the citrate system. Histidine buffer is a preferred buffer system, because acetate buffer systems are not compatible with the lyophilization process.

The term "cryoprotectants" generally includes agents which provide stability to the protein against freezing-induced stresses, presumably by being preferentially excluded from the protein surface. They may also offer protection during primary and secondary drying, and long-term product storage. Examples are polymers such as dextran and polyethylene glycol; sugars such as sucrose, glucose, trehalose, and lactose; surfactants such as polysorbates; and amino acids such as glycine, arginine, and serine.

The terms "lyophilization," "lyophilized," and "freeze-dried" refer to a process by which the material to be dried is first frozen and then the ice or frozen solvent is removed by sublimation in a vacuum environment. An excipient may be included in pre-lyophilized formulations to enhance stability of the lyophilized product upon storage.

The term "lyoprotectant" includes agents that provide stability to the protein during the drying or 'dehydration' process (primary and secondary drying cycles), presumably by providing an amorphous glassy matrix and by binding with the protein through hydrogen bonding, replacing the water molecules that are removed during the drying process. This helps to maintain the protein conformation, minimize protein degradation during the lyophilization cycle and improve the long-term product stability. Examples include polyols or sugars such as sucrose and trehalose.

The term "pharmaceutical formulation" refers to preparations which are in such form as to permit the active ingredients to be effective, and which contains no additional components which are toxic to the subjects to which the formulation would be administered.

"Pharmaceutically acceptable" excipients (vehicles, additives) are those which can reasonably be administered to a subject mammal to provide an effective dose of the active ingredient employed.

"Reconstitution time" is the time that is required to rehydrate a lyophilized formulation with a solution to a particle-free clarified solution.

A "stable" formulation is one in which the protein therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period.

A "stable" lyophilized antibody formulation is a lyophilized antibody formulation with no significant changes observed at a refrigerated temperature (2-8° C.) for at least 12 months, preferably 2 years, and more preferably 3 years; or at room temperature (23-27° C.) for at least 3 months, preferably 6 months, and more preferably 1 year. Typical acceptable criteria for stability are as follows. No more than 10%, preferably 5%, of antibody monomer is degraded as measured by SEC-HPLC. The rehydrated solution is typically colorless, or clear to slightly opalescent by visual analysis. The concentration, pH and osmolality of the formulation have no more than $^{+/-}10\%$ change. Potency is typically within a range of 50-150% of the reference. No more than 10%, preferably 5% of clipping is observed. No more than 10%, preferably 5% of aggregation is formed.

A "stable" pharmaceutical antibody formulation (including a lyophilized formulation, a reconstituted liquid, as well as a liquid formulation that is a "final" formulation (i.e., has not been previously lyophilized)) is a pharmaceutical antibody formulation with no significant changes observed at a refrigerated temperature (2-8° C.) for at least 3 months, preferably 6 months, and more preferably 1 year, and even more preferably up through 2 years. Additionally, a "stable" liquid formulation includes one that exhibits desired features at temperatures including at 25° C. and 40° C. for periods including 1 month, 3 months, 6 months, 12 months, and/or 24 months. Typical acceptable criteria for stability stability are as follows. Typically, no more than about 10%, preferably about 5%, of antibody monomer is degraded as measured by SEC-HPLC. The pharmaceutical antibody formulation is colorless, or clear to slightly opalescent by visual analysis. The concentration, pH and osmolality of the formulation have no more than $^{+/-}10\%$ change. Potency is typically within 50-150 of the reference. Typically, no more than about 10%, preferably about 5% of clipping is observed. Typically, no more than about 10%, preferably about 5% of aggregation is formed.

An antibody "retains its physical stability" in a pharmaceutical formulation if it shows no significant increase of aggregation, precipitation and/or denaturation upon visual examination of color and/or clarity, or as measured by UV light scattering, size exclusion chromatography (SEC) and dynamic light scattering. The changes of protein conformation can be evaluated by fluorescence spectroscopy, which determines the protein tertiary structure, and by FTIR spectroscopy, which determines the protein secondary structure.

An antibody "retains its chemical stability" in a pharmaceutical formulation, if it shows no significant chemical alteration. Chemical stability can be assessed by detecting and quantifying chemically altered forms of the protein. Degradation processes that often alter the protein chemical structure include hydrolysis or clipping (evaluated by methods such as size exclusion chromatography and SDS-PAGE), oxidation (evaluated by methods such as by peptide mapping in conjunction with mass spectroscopy or MALDI/TOF/MS), deamidation (evaluated by methods such as ion-exchange chromatography, capillary isoelectric focusing, peptide mapping, isoaspartic acid measurement), and isomerization (evaluated by measuring the isoaspartic acid content, peptide mapping, etc.).

An antibody "retains its biological activity" in a pharmaceutical formulation, if the biological activity of the antibody at a given time is within a predetermined range of the biological activity exhibited at the time the pharmaceutical formulation was prepared. The biological activity of an antibody can be determined, for example, by an antigen binding assay.

The term "isotonic" means that the formulation of interest has essentially the same osmotic pressure as human blood. Isotonic formulations will generally have an osmotic pressure from about 270-328 mOsm. Slightly hypotonic pressure is 250-269 and slightly hypertonic pressure is 328-350 mOsm.

Osmotic pressure can be measured, for example, using a vapor pressure or ice-freezing type osmometer.

Tonicity Modifiers: Salts (NaCl, KCl, $MgCl_2$, $CaCl_2$, etc.) are used as tonicity modifiers to control osmotic pressure. In addition, cryprotecants/lyoprotectants and/or bulking agents such as sucrose, mannitol, glycine etc. can serve as tonicity modifiers.

Analytical Methods

Analytical methods suitable for evaluating the product stability include size exclusion chromatography (SEC), dynamic light scattering test (DLS), differential scanning calorimetery (DSC), iso-asp quantification, potency, UV at 340 nm, UV spectroscopy, and FTIR. SEC (J. Pharm. Scien., 83:1645-1650, (1994); Pharm. Res., 11:485 (1994); J. Pharm. Bio. Anal., 15:1928 (1997); J. Pharm. Bio. Anal., 14:1133-1140 (1986)) measures percent monomer in the product and gives information of the amount of soluble aggregates. DSC (Pharm. Res., 15:200 (1998); Pharm. Res., 9:109 (1982)) gives information of protein denaturation temperature and glass transition temperature. DLS (American Lab., November (1991)) measures mean diffusion coefficient, and gives information of the amount of soluble and insoluble aggregates. UV at 340 nm measures scattered light intensity at 340 nm and gives information about the amounts of soluble and insoluble aggregates. UV spectroscopy measures absorbance at 278 nm and gives information of protein concentration. FTIR (Eur. J. Pharm. Biopharm., 45:231 (1998); Pharm. Res., 12:1250 (1995); J. Pharm. Scien., 85:1290 (1996); J. Pharm. Scien., 87:1069 (1998)) measures IR spectrum in the amide one region, and gives information of protein secondary structure.

The iso-asp content in the samples is measured using the Isoquant Isoaspartate Detection System (Promega). The kit uses the enzyme Protein Isoaspartyl Methyltransferase (PIMT) to specifically detect the presence of isoaspartic acid residues in a target protein. PIMT catalyzes the transfer of a methyl group from S-adenosyl-L-methionine to isoaspartic acid at the .alpha.-carboxyl position, generating S-adenosyl-L-homocysteine (SAH) in the process. This is a relatively small molecule, and can usually be isolated and quantitated by reverse phase HPLC using the SAH HPLC standards provided in the kit.

The potency or bioidentity of an antibody can be measured by its ability to bind to its antigen. The specific binding of an antibody to its antigen can be quantitated by any method known to those skilled in the art, for example, an immunoassay, such as ELISA (enzyme-linked immunosorbant assay).

A "reconstituted" formulation is one that has been prepared by dissolving a lyophilized protein formulation in a diluent such that the protein is dispersed in the reconstituted formulation. The reconstituted formulation is suitable for administration, e.g. parenteral administration), and may optionally be suitable for subcutaneous administration.

Humanized Anti-PD-1 Antibodies

DNA constructs encoding the variable regions of the heavy and light chains of the humanized antibodies h409A11, h409A16 and h409A17 are described in WO2008/156712.

The foregoing written specification is considered to be sufficient to enable one skilled in the art to practice the invention. The present invention is not to be limited in scope by the culture deposited, since the deposited embodiment is intended as a single illustration of one aspect of the invention and any culture that is functionally equivalent is within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

Sequences are provided for exemplary anti-human PD-1 antibodies; a summary table of the sequences is provided in Table 6. CDRs are provided under separate sequence identifiers, as indicated in Table 2 for h409A11.

Ordinarily, amino acid sequence variants of the humanized anti-PD-1 antibody will have an amino acid sequence having at least 75% amino acid sequence identity with the original humanized antibody amino acid sequences of either the heavy or the light chain more preferably at least 80%, more preferably at least 85%, more preferably at least 90%, and most preferably at least 95, 98, or 99%. Identity or homology with respect to this sequence is defined herein as the percentage of amino acid residues in the candidate sequence that are identical with the humanized anti-PD-1 residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

The humanized antibody can be selected from any class of immunoglobulins, including IgM, IgG, IgD, IgA, and IgE. Preferably, the antibody is an IgG antibody. Any isotype of IgG can be used, including $IgG_1$, $IgG_2$, $IgG_3$, and $IgG_4$. Different constant domains may be appended to the humanized $V_L$ and $V_H$ regions provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

Likewise, either class of light chain can be used in the compositions and methods herein. Specifically, kappa, lambda, or variants thereof are useful in the present compositions and methods.

CDR and FR residues are determined according to the standard sequence definition of Kabat. Kabat et al. (1987) Sequences of Proteins of Immunological Interest, National Institutes of Health, Bethesda Md.

The signal sequences, or nucleic acid sequences encoding the signal sequences, may be appended to the N-terminus of the respective antibody chains to create a precursor protein for secretion from a host cell. Alternative signal sequences may also be used, and several can be found at "SPdb: a Signal Peptide Database." Choo et al. (2005) *BMC Bioinformatics* 6:249.

TABLE 2

H409A11 CDR Sequences

| Antibody | CDR Sequence | SEQ ID NO: |
|---|---|---|
| H409A11 | Light chain CDR1 (equivalent to hPD-1.09A light chain CDR1) RASKGVSTSGYSYLH | 15 |

TABLE 2-continued

H409A11 CDR Sequences

| Antibody | CDR Sequence | SEQ ID NO: |
|---|---|---|
| H409A11 | Light chain CDR2 (equivalent to hPD-1.09A light chain CDR2) LASYLES | 16 |
| H409A11 | Light chain CDR3 (equivalent to hPD-1.09A light chain CDR3) QHSRDLPLT | 17 |
| H409A11 | Heavy chain CDR1 (equivalent to hPD-1.09A heavy chain CDR1) NYYMY | 18 |
| H409A11 | Heavy chain CDR2 (equivalent to hPD-1.09A heavy chain CDR2) GINPSNGGTNFNEKFKN | 19 |
| H409A11 | Heavy chain CDR3 (equivalent to hPD-1.09A heavy chain CDR3) RDYRFDMGFDY | 20 |

Biological Activity of Humanized Anti-PD-1

Formulations of the present invention include antibodies and fragments thereof that are biologically active when reconstituted or in liquid form. As used herein, the term "biologically active" refers to an antibody or antibody fragment that is capable of binding the desired the antigenic epitope and directly or indirectly exerting a biologic effect. Typically, these effects result from the failure of PD-1 to bind its ligands. As used herein, the term "specific" refers to the selective binding of the antibody to the target antigen epitope. Antibodies can be tested for specificity of binding by comparing binding to PD-1 to binding to irrelevant antigen or antigen mixture under a given set of conditions.

Lyophilized Pharmaceutical Compositions

Lyophilized formulations of therapeutic proteins provide several advantages. Lyophilized formulations in general offer better chemical stability than solution formulations, and thus increased half-life. A lyophilized formulation may also be reconstituted at different concentrations depending on clinical factors, such as route of administration or dosing. For example, a lyophilized formulation may be reconstituted at a high concentration (i.e. in a small volume) if necessary for subcutaneous administration, or at a lower concentration if administered intravenously. High concentrations may also be necessary if high dosing is required for a particular subject, particularly if administered subcutaneously where injection volume must be minimized. One such lyophilized antibody formulation is disclosed at U.S. Pat. No. 6,267,958, which is hereby incorporated by reference in its entirety. Lyophilized formulations of another therapeutic protein are disclosed at U.S. Pat. No. 7,247,707, which is hereby incorporated by reference in its entirety.

Typically, the lyophilized formulation is prepared in anticipation of reconstitution at high concentration of drug product (DP, in an exemplary embodiment humanized anti-PD-1 antibody h409A11, or antigen binding fragment thereof), i.e. in anticipation of reconstitution in a low volume of water. Subsequent dilution with water or isotonic buffer can then readily be used to dilute the DP to a lower concentration. Typically, excipients are included in a lyophilized formulation of the present invention at levels that will result in a roughly isotonic formulation when reconstituted at high DP concentration, e.g. for subcutaneous administration. Reconstitution in a larger volume of water to give a lower DP concentration will necessarily reduce the tonicity of the reconstituted solution, but such reduction may be of little significance in non-subcutaneous, e.g. intravenous, administration. If isotonicity is desired at lower DP concentration, the lyophilized powder may be reconstituted in the standard low volume of water and then further diluted with isotonic diluent, such as 0.9% sodium chloride.

In an embodiment of the present invention, humanized anti-PD-1 antibody (or antigen binding fragment thereof) is formulated as a lyophilized powder for reconstituting and utilizing for intravenous administration. Exemplary formulations are described in Tables 3-4, and in FIGS. 1-9. In certain embodiments, the antibody (or antigen binding fragment thereof) is provided at about 50 mg/vial, and is reconstituted with sterile water for injection prior to use. If desired, the reconstituted antibody may be aseptically diluted with 0.9% Sodium Chloride Injection USP in a sterile IV container. The target pH of the reconstituted formulation is 5.5±0.5. In various embodiments, the lyophilized formulation of the present invention enables reconstitution of the anti-PD-1 antibody to high concentrations, such as about 20, 25, 30, 40, 50, 60, 75, 100 or more mg/mL.

The present invention provides in certain embodiments, a lyophilized formulation comprising humanized anti-PD-1 antibody, a histidine buffer at about pH 5.5, or at about pH 5.0, for example at about 5.1, 5.2, 5.3, 5.4, 5.6, 5.7, 5.8, 5.9, or 6.0.

When a range of pH values is recited, such as "a pH between pH 5.5 and 6.0," the range is intended to be inclusive of the recited values. Unless otherwise indicated, the pH refers to the pH after reconstitution of the lyophilized formulations of the present invention. The pH is typically measured at 25° C. using standard glass bulb pH meter. As used herein, a solution comprising "histidine buffer at pH X" refers to a solution at pH X and comprising the histidine buffer, i.e. the pH is intended to refer to the pH of the solution.

The formulation in Table 3 reflects the weight of the components in a batch formulation, as lyophilized in vials, and as reconstituted. Lyophilized formulations are by definition essentially dry, and thus the concept of concentration is not useful in describing them. Describing a lyophilized formulation in the terms of the weight of the components in a unit dose vial is more useful, but is problematic because it varies for different doses or vial sizes. In describing the lyophilized formulations of the present invention, it is useful to express the amount of a component as the ratio of the weight of the component compared to the weight of the drug substance (DS) in the same sample (e.g. a vial). This ratio may be expressed as a percentage. Such ratios reflect an intrinsic property of the lyophilized formulations of the present invention, independent of vial size, dosing, and reconstitution protocol.

In other embodiments, the lyophilized formulation of anti-human PD-1 antibody, or antigen binding fragment, is defined in terms of the pre-lyophilization solution used to make the lyophilized formulation, such as the pre-lyophilization solution. In one embodiment the pre-lyophilization solution comprises antibody, or antigen-binding fragment thereof, at a concentration of about 25 mg/mL. Such pre-lyophilization solutions may be at pH 4.4-5.2 (including about 4.4, 4.5, 4.6, 4.7, 4.8, 4.9, 5.0, 5.1. and 5.2), e.g. preferably about pH 4.8, or about pH 5.5.

In yet other embodiments, the lyophilized formulation of anti-human PD-1 antibody, or antigen binding fragment, is defined in terms of the reconstituted solution generated from the lyophilized formulation, such as the reconstituted solution disclosed at Table 4.

Reconstituted solutions may comprise antibody, or antigen-binding fragment thereof, at concentrations of about 10, 15, 20, 25, 30, 40, 50, 60, 75, 80, 90 or 100 mg/mL or higher concentrations such as 150 mg/mL, 200 mg/mL, 250 mg/mL, or up to about 300 mg/mL. Such reconstituted solutions may be at about pH 5.5, or range from about pH 5.0 to about 6.0

The lyophilized formulations of the present invention are formed by lyophilization (freeze-drying) of a pre-lyophilization solution. Freeze-drying is accomplished by freezing the formulation and subsequently subliming water at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will dictate the time required for drying, which can range from a few hours to several days (e.g. 40-60 hrs). A secondary drying stage may be carried out at about 0-40° C., depending primarily on the type and size of container and the type of protein employed. The secondary drying time is dictated by the desired residual moisture level in the product and typically takes at least about 5 hours. Typically, the moisture content of a lyophilized formulation is less than about 5%, and preferably less than about 3%. The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial.

The lyophilized formulations of the present invention are reconstituted prior to administration. The protein may be reconstituted at a concentration of about 10, 15, 20, 25, 30, 40, 50, 60, 75, 80, 90 or 100 mg/mL or higher concentrations such as 150 mg/mL, 200 mg/mL, 250 mg/mL, or 300 mg/mL up to about 500 mg/mL. High protein concentrations are particularly useful where subcutaneous delivery of the reconstituted formulation is intended. However, for other routes of administration, such as intravenous administration, lower concentrations of the protein may be desired (e.g. from about 5-50 mg/mL).

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution.

The lyophilized formulations of the present invention are expected to be stable for at least about 36 months (based on the stability data from FIGS. 1-9). In addition, the liquid formulation is expected to exhibit stability for at least 24 months, based on 24 months of stability data from reconstituted h409A11 formulation in polypropylene tubes at 2-8° C.

In line with the results shown in FIGS. 1-9, stability has been observed through 2 years for a refrigerated reconstituted formulation of h409A11. 2 mL samples in polypropylene tubes were stored at 5° C., and 25H and RH4 conditions and tested at initial, 1, 3, 6, 9, 12, 18, and 24 month periods. This reconstituted h409A11 formulation has the same substituents in the same concentration as a liquid h409A11 formulation (i.e., a formulation that was not lyophilized) and the stability is expected to be the same.

Liquid Pharmaceutical Compositions

A liquid antibody formulation can be made by taking the drug substance (e.g., anti-humanized PD-1) which is in liquid form (e.g., h409A11 in an aqueous pharmaceutical formulation) and buffer exchanging it into the desired buffer as the last step of the purification process. There is no lyophilization step in this embodiment. The drug substance in the final buffer is concentrated to a desired concentration. Excipients such as sucrose and polysorbate 80 are added to the drug substance and it is diluted using the appropriate buffer to final protein concentration. The final formulated drug substance is filtered using 0.22 μm filters and filled into a final container (e.g. glass vials). Such a liquid formulation is exemplified by a final liquid formulation comprising 10 mM histidine pH 5.5, 7% sucrose, 0.02% polysorbate 80, and 25 mg/mL h409A11.

Various literature references are available to facilitate selection of pharmaceutically acceptable carriers or excipients. See, e.g., *Remington's Pharmaceutical Sciences and U.S. Pharmacopeia: National Formulary*, Mack Publishing Company, Easton, Pa. (1984); Hardman et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.

Toxicity is a consideration in selecting the proper dosing of a therapeutic agent, such as a humanized anti-PD-1 antibody (or antigen binding fragment thereof). Toxicity and therapeutic efficacy of the antibody compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio of $LD_{50}$ to $ED_{50}$. Antibodies exhibiting high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

Suitable routes of administration may, for example, include parenteral delivery, including intramuscular, intradermal, subcutaneous, intramedullary injections, as well as intrathecal, direct intraventricular, intravenous, intraperitoneal. Drugs can be administered in a variety of conventional ways, such as intraperitoneal, parenteral, intraarterial or intravenous injection. Modes of administration in which the volume of solution must be limited (e.g. subcutaneous administration) require a lyophilized formulation to enable reconstitution at high concentration.

Alternately, one may administer the antibody in a local rather than systemic manner, for example, via injection of the antibody directly into a pathogen-induced lesion characterized by immunopathology, often in a depot or sustained release formulation. Furthermore, one may administer the antibody in a targeted drug delivery system, for example, in a liposome coated with a tissue-specific antibody, targeting, for example, pathogen-induced lesion characterized by immunopathology. The liposomes will be targeted to and taken up selectively by the afflicted tissue.

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348: 601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002).

Determination of the appropriate dose is made by the clinician, e.g., using parameters or factors known or suspected in the art to affect treatment or predicted to affect treatment. The appropriate dosage ("therapeutically effective amount") of the protein will depend, for example, on the condition to be treated, the severity and course of the condition, whether the protein is administered for preventive or therapeutic purposes, previous therapy, the patient's clinical history and response to the protein, the type of protein used, and the discretion of the attending physician. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. The antibody is suitably administered to the patient at one time or repeatedly. The antibody may be administered alone or in conjunction with other drugs or therapies.

A pharmaceutical antibody formulation can be administered by continuous infusion, or by doses at intervals of, e.g., one day, 1-7 times per week, one week, two weeks, three weeks, monthly, bimonthly, etc. A preferred dose protocol is one involving the maximal dose or dose frequency that avoids significant undesirable side effects. A total weekly dose is generally at least 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346:1692-1698; Liu et al. (1999) *J. Neurol. Neurosurg. Psych.* 67:451-456; Portielji et al. (20003) *Cancer Immunol. Immunother.* 52:133-144. The desired dose of a small molecule therapeutic, e.g., a peptide mimetic, natural product, or organic chemical, is about the same as for an antibody or polypeptide, on a moles/kg basis.

In certain embodiments, dosing will comprise administering to a subject escalating doses of 1.0, 3.0, and 10 mg/kg of the pharmaceutical formulation, i.e, a formulation comprising h409A11, over the course of treatment. The formulation comprising h409A11 can be a reconstituted liquid formulation, or it can be a liquid formulation not previously lyophilized. Time courses can vary, and can continue as long as desired effects are obtained. In certain embodiments, dose escalation will continue up to a dose of about 10 mg/kg. In certain embodiments, the subject will have a histological or cytological diagnosis of melanoma, or other form of solid tumor, and in certain instances, a subject may have non-measurable disease. In certain embodiments, the subject will have been treated with other chemotherapeutics, while in other embodiments, the subject will be treatment naïve.

In yet additional embodiments, the dosing regimen will comprise administering a dose of 1, 3, or 10 mg/kg of any of the pharmaceutical formulations described herein (i.e, a formulation comprising h409A 11), throughout the course of treatment. For such a constant dosing regimen, the interval between doses will be about 14 days (±2 days). In certain embodiments, the interval between doses will be about 21 days (±2 days).

In certain embodiments, the dosing regimen will comprise administering a dose of from about 0.005 mg/kg to about 10 mg/kg, with intra-patient dose escalation. In certain embodiments, a dose of 5 mg/kg or 10 mg/kg will be administered at intervals of every 3 weeks, or every 2 weeks. In yet additional embodiments, a dose of 3 mg/kg will be administered at three week intervals for melanoma patients or patients with other solid tumors. In these embodiments, patients should have non-resectable disease; however, patients may have had previous surgery.

In certain embodiments, a subject will be administered a 30 minute IV infusion of any of the pharmaceutical formulations described herein. In certain embodiments for the escalating dose, the dosing interval will be about 28 days ((±1 day) between the first and second dose. In certain embodiments, the interval between the second and third doses will be about 14 days (±2 days). In certain embodiments, the dosing interval will be about 14 days (±2 days), for doses subsequent to the second dose.

In certain embodiments, the use of cell surface markers and/ore cytokine markers, as described in co-pending patent publications WO2012/018538 or WO2008/156712 will be used in bioassays for monitoring, diagnostic, patient selection, and/or treatment regimens involving blockade of the PD-1 pathway.

Subcutaneous administration may performed by injected using a syringe, or using other injection devices (e.g. the Inject-ease® device); injector pens; or needleless devices (e.g. MediJector and BioJector®).

The broad scope of this invention is best understood with reference to the following examples, which are not intended to limit the inventions to the specific embodiments. The specific embodiments described herein are offered by way of example only, and the invention is to be limited by the terms of the appended claims, along with the full scope of equivalents to which such claims are entitled.

EXAMPLES

Example 1

Antibody Production h409A11 is a humanized monoclonal antibody that binds to human PD-1 and blocks the interaction between PD-1 and its ligands PDL1 and PDL2. The antibody is an IgG4/kappa isotype with a stabilizing S228P sequence alteration in the Fc region. Table 2 provides a list of the CDR sequences. The theoretical molecular weights of the heavy and light chains derived from the amino acid sequences, excluding glycosylation, are 49.3 kDa and 23.7 kDa, respectively. The parental antibody (hPD-1.09A) was produced by immunizing mice with hPD-1 DNA. The h409A11 antibody was generated by humanization of the parental murine anti-human PD-1 antibody by the Medical Research Council (Cambridge, UK) using CDR grafting technology, (e.g., U.S. Pat. No. 5,225, 539), as described in co-pending WO2008/156712.

An expression plasmid was constructed for expression of heavy and light chains of h409A11. The nucleotide sequences encoding the heavy and light chains, along with their respective promoters and poly A signal sequence, were confirmed by DNA sequence analysis. The expression vector was subsequently used to transfect a CHO cell line. An antibody-expressing clone was selected for the generation of a Master Seed Bank (MSB), based on growth, productivity, and production stability. This MSB was then used to prepare the antibody and to generate the Master Cell Bank (MCB).

Cells from the MCB were expanded in shake flasks, culture bags, and a seed bioreactor to generate the inoculum for a production bioreactor to produce the antibody product. Further processing included three chromatography steps (protein A affinity, cation exchange and anion exchange chromatography), two orthogonal viral clearance steps (low pH viral inactivation and viral reduction filtration), ultrafiltration/diafiltration, and a final 0.2 µm filtration step.

h409A11 Structure and Features h409A11 is a highly selective humanized monoclonal antibody that blocks the interaction between human PD-1 and its ligands PD-L1 and PD-L2. h409A11 is heterogeneously glycosylated at asparagine 297 within the Fc domain of each heavy chain, yielding molecular weights typically ranging between 148.9 and 149.5 kDa, depending on the attached glycan chains. The amino acid sequences of the heavy and light chains of h409A11 are found in SEQ ID NO:31 and SEQ ID NO:36. The light chain without the leader sequences comprises amino acid residues 20 to 237 of SEQ ID NO: 36 and the heavy chain without the leader sequences comprises amino acid residues 20 to 466 of SEQ ID NO: 31.

Stable Humanized PD-1 Formulations

In certain embodiments, stable humanized PD-1 e.g., h409A11 is an aqueous solution stored under refrigerated conditions (temp. range: typically about 2-8° C., but under certain circumstances, the aqueous formulation may exhibit stability at other temperatures including at about 25° C. and about 40° C. for periods of up to about 12 months) at a concentration of ≥25 mg/mL in 10 mM Histidine buffer, pH 5.0-6.0. In certain embodiments, stable humanized PD-1 e.g., h409A11 is an aqueous solution at a concentration of about 25 mg/mL in 10 mM Histidine buffer, pH 5.0-6.0. The stable formulation (i.e., drug substance) is typically a clear to opalescent solution and may contain particulates.

In certain embodiments, a liquid or frozen solution of h409A11 is formulated in histidine buffer (pH 5.5) containing sucrose and polysorbate 80.

An additional exemplary formulation includes: h409A11 formulated in histidine buffer (pH 5.5) containing sucrose and polysorbate 80 in lyophilized form.

In certain embodiments, stable humanized PD-1 formulation is provided as lyophilized powder in vials intended for single-use.

In certain embodiments, stable humanized PD-1 formulation is reconstituted with water for injection (WFI) and aseptically diluted with appropriate volumes of 0.9% sodium chloride for injection in a sterile IV container to form an admixture solution.

Biological Activity

Biological activity of the humanized anti-PD-1 antibody is measured by its ability to compete with PD-L1 (natural ligand of PD-1) in binding to human PD-1, quantified in competitive ELISA relative to a reference material. The stable formulations described herein exhibit biological activity for long periods of time, including up to at least about eighteen months. The stability of several batches of h409A11, under various storage conditions are illustrated in FIGS. 1-9.

Stable Formulations of Humanized Anti-PD-1 Antibodies

Lyophilized formulations of anti-PD-1 antibody are prepared as follows. An exemplary batch formula for h409A11 antibody is provided in Table 3. The final concentration of antibody is 25 mg/mL. This batch formulation may be used to prepare the lyophilized 50 mg/vial units, as discussed with reference to Table 4, infra. Polysorbate 80 from a vegetable source is used. Additional hydrochloric acid or sodium hydroxide may be added to adjust the pH to the desired value of approximately 5.5 (±0.2). The components are brought to a final volume of 14 L with sterile water for injection (WFI). Correspondingly smaller lots may be prepared by proportional reduction of the amounts listed in Table 3.

An exemplary liquid antibody formulation is prepared by taking the drug substance (e.g., anti-humanized PD-1 from a batch formula described herein) which is in liquid form (e.g., h409A11 in an aqueous formulation) and buffer exchanging it into the desired buffer as the last step of the purification process. In this instance, there is no previous lyophilization step. The drug substance in the final histidine buffer is concentrated to a desired concentration. Excipients such as sucrose and polysorbate 80 are added to the drug substance and it is diluted using the appropriate buffer to final protein concentration. The final formulated drug substance is filtered using 0.22 µm filters and filled into a final container (e.g. glass vials). Such a liquid formulation includes final liquid formulation comprising 10 mM histidine pH 5.5, 7% sucrose, 0.02% polysorbate 80, and 25 mg/mL h409A11.

TABLE 3

Batch Formula of Representative 14.0 L Pre-lyophilization Solution for h409A11 Powder for Injection, 50 mg/vial

| Component | Compendial Grade | Concentration (mg/mL) | Amount per Batch (g) |
|---|---|---|---|
| h409A11 antibody | N/A | 25.0 | 350.0 |
| L-Histidine | USP | 1.55 | 21.7 |
| Polysorbate 80 | NF | 0.2 | 2.8 |
| Sucrose | NF | 70 | 980 |
| Hydrochloric acid [a] | NF | — | — |
| Sodium Hydroxide [a] | NF | — | pH adjustment |
| Water for injection [b] | USP | — | 14.0 L @ q.s |

[a] Hydrochloric acid and sodium hydroxide added if needed to adjust pH to 5.5
[b] Water removed by sublimation and desorption during lyophilization The unit composition of an exemplary final lyophilized formulation of humanized anti-PD-1 is provided at Table 4.

TABLE 4

Unit Composition of Lyophilized Powder Formulation for Injection, 50 mg/vial

| Component | Grade | Amount (mg/vial) | Concentration after Reconstitution (mg/mL)[b] | Function |
|---|---|---|---|---|
| h409A11 | N/A | 50 | 25 | Drug Substance/Active Pharmaceutical ingredient |
| L-Histidine | USP | 3.1 | 1.55 | Buffer |
| Polysorbate 80 | NF | 0.4 | 0.2 | Surfactant |
| Sucrose | NF | 140 | 70 | Stabilizer/Tonicity Modifier |
| Hydrochloric acid [C] | NF | — | — | pH adjustment |
| Sodium Hydroxide [C] | NF | — | — | pH adjustment |
| Sterile Water for Injection (sWFI or WFI)[d] | USP | 2.0 mL @ q.s. | — | Solvent |

[a] An excess fill of 0.4 mL is provided to ensure the recovery of 50 mg h409A11 per vial.
[b] Following reconstitution with 2.3 mL sterile water for injection.
[C] Hydrochloric acid and sodium hydroxide added if needed to adjust pH to 5.5
[d] Water removed by sublimation and desorption during lyophilization The unit formulation of Table 4 comprises $1/20,000^{th}$ of the batch formulation of Table 3 after lyophilization to remove the water. The 50 mg of DS is added as 2.0 mL of the 25 mg/mL batch formulation of Table 3. Each vial is filled with 2.4 mL and reconstituted with 2.3 mL sWFI, resulting in approximately 2.4 mL of reconstituted solution due to expansion volume of the lyophilized cake.

The drug is packaged in sterile 20 mm neck, 6R DIN, Type 1 glass tubing vials, closed with 20-mm gray butyl rubber stoppers and sealed with aluminum crimp seals. Vials are stored at 2-8° C., and refrigerated when shipped.

Compounding involves the following steps. Charge the required amount of water for injection (WFI) into a tared compounding vessel. Charge and dissolve with mixing, sucrose, histidine, and polysorbate 80 from a vegetable source. Measure the pH and adjust if needed to bring the pH to about 5.4-5.6. Use hydrochloric acid and/or sodium hydroxide to adjust the pH. Equilibrate the drug substance to ambient temperature and charge the drug substance slowly into the compounding vessel. Continue to mix gently to avoid foaming. Measure the pH again and adjust if needed to bring the pH to approximately 5.5. Charge WFI to the final weight of the bulk solution with continued gentle mixing.

Filtration involves the following steps. Connect clarifying filter (0.22 μm) and sterilizing filter (0.22 μm) to the compounding vessel. Collect an aliquot of the bulk solution for bioburden testing after clarifying filtration step. Perform aseptic filtration using a 0.22 μm filter into a sterile container. Remove aliquot of sample after aseptic filtration for bulk sterility testing. Perform filter integrity testing after product filtration.

Filling involves the following steps. Using suitable filling equipment, aseptically fill the product solution into sterilized Type I tubing glass vials to achieve a target fill volume of 2.4 mL. Perform fill weight checks during filling. Partially seat sterilized lyo-shape stoppers into filled vials. Load the filled vials into a suitable freeze-dryer.

Lyophilization, stoppering and capping involve the following steps. Lyophilize the filled vials using an appropriate lyophilization cycle. After lyophilization is complete, backfill the vials with 0.22 μm filtered nitrogen and fully stopper. Unload the stoppered vials from the lyophilizer and seal them.

The resulting vials are inspected for visual defects and stored at 2-8° C. Finished unit dosage vials are shipped under refrigerated conditions.

Example 2

Stability Testing of Lyophilized Formulations of Humanized Anti-PD-1 Antibodies

FIGS. 1-9 provide data of stability testing of lyophilized formulations of a humanized anti-human PD-1 antibody under various storage conditions. Vials were stored in upright configurations. As discussed in more detail below, formulations of the present invention show stability through at least 24 months for antibodies lyophilized at pH 5.5 (histidine buffer), as well as similar liquid formulations.

Stability was assessed as follows. Samples were lyophilized in 6R DIN Type I glass vials, and sealed with 20 mm bromobutyl lyo stoppers (Helvoet Rubber & Plastic Technologies BV, Helleovoetsluis, The Netherlands) and flip-off aluminum seals. Vials were placed on stability stations under the following storage conditions: 5° C. (5±3° C.), 25H (25, 60% relative humidity), or RH4 (40° C., 70% relative humidity). Samples were obtained at an initial time point, and for certain samples at a variety of time points including 1, 2, 3, 6, 9, 12, 18, and 24 months.

The stability of the samples is illustrated by the various characteristics presented in the tables in FIGS. 1-9. The lyophilized samples were visually inspected, reconstituted, and the reconstituted formulation was visually inspected. The pH of the samples after reconstitution was measured, and the protein concentration determined by U.V. absorbance. The samples were analyzed by CE-SDS technique in which protein was denatured with sodium dodecyl sulfate (SDS) under reducing and non-reducing conditions and separated using capillary electrophoresis (CE). The proteins separate based on their apparent molecular weight. Under non-reducing conditions, all species other than the main IgG peak are classified as impurities. Under reducing conditions, the IgG is resolved into the heavy and light chains. All other species are classified as impurities.

Purity of the sample was further assessed by high performance size exclusion chromatography (HPSEC) in which the percentage of monomer was determined, as well as the percentages of high molecular weight species (possibly aggregates) and late eluting peaks (possibly degradation products).

Additional sample characterization data are provided in FIGS. 1-9. High performance ion-exchange chromatography (HP-IEX) was used to assess purity by revealing the presence of acidic or basic variants. Results are presented as a percentage of total observed material. The samples were further characterized for biological function using an enzyme-linked immunosorbent assay (ELISA) for binding to human PD-1. The antibody concentration necessary to achieve half-maximal binding is called $EC_{50}$. Potency of the test sample was assessed by comparing binding curves of the test samples to a reference material (or control) by the ration of $EC_{50}$'s. Potency was expressed as percent relative potency of reference material (or control). Moisture content of the lyophilized powder was also determined by coulometric titration. Particulate matter count measurements were performed to count particles ≥10 μm and ≥25 μm. The method used for these measurements was based on USP<788>.

These results demonstrate high stability formulations of the present invention over at least 24 months at about pH 5.5.

The data reveal no trending over time that would reflect instability for samples the tested storage conditions.

Example 3

Initial Clinical Results

Phase 1 Study of h409A11 (Anti-PD-1 Monoclonal Antibody) in Patients with Advanced Solid Tumors A phase 1 trial examined safety, PK, PD, and antitumor activity of h409A11. An open-label, dose escalation study was conducted in patients with advanced malignancy refractory to standard chemotherapy. In the initial patient set, patients with advanced solid tumors were treated with a stable h409A11 formulation as described herein. There was no limitation/restriction regarding surgery; however, patients were not currently surgical candidates. Cohorts of 3-6 patients were enrolled (3+3 design) at IV doses of 1, 3, or 10 mg/kg. Following an initial dose and 28-day Cycle 1, patients were allowed to subsequently receive multiple doses given every 2 wks. For phase 1 part A, three patients were treated at 1 mg/kg, three patients were treated at 3 mg/kg, and nine patients were treated at 10 mg/kg and all were dosed every 2 weeks. There was no intrapatient dose escalation. Radiographic assessment was conducted every 8 wks using RECIST 1.1 guidelines.

Nine patients, 3 at each dose level, completed the dose-limiting toxicity (DLT) period (28 d). Patients had non-small cell lung cancer (NSCLC, n=3), rectal cancer (n=2), melanoma (MEL, n=2), sarcoma (n=1), or carcinoid (n=1). To date, a total of 63 doses were administered (median 7/patient; max 12) without DLT. Drug-related adverse events (AEs) across all doses included Grade 1 fatigue (n=3), nausea (n=2), diarrhea (n=1), dysgeusia (n=1), breast pain (n=1), and pruritus (N=1). One drug-related Grade 2 AE of pruritus was reported. No drug-related AEs ≥grade 3 were observed. PK data are shown in Table 5. Based on RECIST, 1 patient with MEL on therapy >6 mths had a partial response, and preliminary evidence of tumor size reduction (stable disease) was observed in 3 additional patients with advanced cancer. These results show that h409A11 was well-tolerated without DLT across 3 tested dose levels. (i.e., 1, 3, and 5 mg/kg). Evidence of antitumor activity was observed.

TABLE 5

Mean (CV %) PK Parameter Values of MK-3475 Following Single IV Dose of 1, 3, or 10 mg/kg in Cycle 1

| Dose (mg/kg) | N | $C_{max}$ (µg/mL) | $AUC_{(0-28day)}$ (µg · day/mL) | $t_{1/2}{}^a$ (day) |
|---|---|---|---|---|
| 1 | 4 | 16.8 (23) | 163 (20)[b] | 15.1 (41)[b] |
| 3 | 3 | 109 (26) | 990 (23) | 21.7 (11) |
| 10 | 2 | 337 (8) | 2640 (30) | 13.6 (28) |

[a]PK sampling up to 28 days following first IV administration, therefore $t_{1/2}$ not fully characterized.
[b]N = 3 due to subject discontinuation.

TABLE 6 provides a brief description of the sequences in the sequence listing.
Sequence Identifiers

| SEQ ID NO: | Description |
|---|---|
| 1 | hPD-1.08A heavy chain variable region (DNA) |
| 2 | hPD-1.08A light chain variable region (DNA) |
| 3 | hPD-1.09A heavy chain variable region (DNA) |
| 4 | hPD-1.09A light chain variable region (DNA) |
| 5 | hPD-1.08A heavy chain variable region (AA) |
| 6 | hPD-1.08A light chain variable region (AA) |
| 7 | hPD-1.09A heavy chain variable region (AA) |
| 8 | hPD-1.09A light chain variable region (AA) |
| 9 | hPD-1.08A light chain CDR1 (AA) |
| 10 | hPD-1.08A light chain CDR2 (AA) |
| 11 | hPD-1.08A light chain CDR3 (AA) |
| 12 | hPD-1.08A heavy chain CDR1 (AA) |
| 13 | hPD-1.08A heavy chain CDR2 (AA) |
| 14 | hPD-1.08A heavy chain CDR3 (AA) |
| 15 | hPD-1.09A light chain CDR1 (AA) |
| 16 | hPD-1.09A light chain CDR2 (AA) |
| 17 | hPD-1.09A light chain CDR3 (AA) |
| 18 | hPD-1.09A heavy chain CDR1 (AA) |
| 19 | hPD-1.09A heavy chain CDR2 (AA) |
| 20 | hPD-1.09A heavy chain CDR3 (AA) |
| 21 | 109A-H heavy chain variable region (DNA) |
| 22 | Codon optimized 109A-H heavy chain variable region (DNA) |
| 23 | Codon optimized 409A-H heavy chain full length (DNA) |
| 24 | K09A-L-11 light chain variable region (DNA) |
| 25 | K09A-L-16 light chain variable region (DNA) |
| 26 | K09A-L-17 light chain variable region (DNA) |
| 27 | Codon optimized K09A-L-11 light chain variable region (DNA) |
| 28 | Codon optimized K09A-L-16 light chain variable region (DNA) |
| 29 | Codon optimized K09A-L-17 light chain variable region (DNA) |
| 30 | 109A-H heavy chain variable region (AA) |
| 31 | 409A-H heavy chain full length (AA) |
| 32 | K09A-L-11 light chain variable region (AA) |
| 33 | K09A-L-16 light chain variable region (AA) |
| 34 | K09A-L-17 light chain variable region (AA) |
| 35 | 109A-H heavy chain full length (AA) |
| 36 | K09A-L-11 light chain full length (AA) |
| 37 | K09A-L-16 light chain full length (AA) |
| 38 | K09A-L-17 light chain full length (AA) |

As used herein, including the appended claims, the singular forms of words such as "a," "an," and "the," include their corresponding plural references unless the context clearly dictates otherwise. Unless otherwise indicated, the proteins and subjects referred to herein are human proteins and subject, rather than another species.

REFERENCES

1. Sharpe, A. H, Wherry, E. J., Ahmed R., and Freeman G. J. The function of programmed cell death 1 and its ligands in regulating autoimmunity and infection. *Nature Immunology* (2007); 8:239-245.
2. Greenwald R. J., Freeman G. J., and Sharpe A. H. The B7 family revisited. *Annual Reviews of Immunology* (2005); 23:515-548.
3. Okazaki T and Honjo T. PD-1 and PD-1 ligands: from discovery to clinical application. *International immunology* (2007); 19:813-824.
4. Chemnitz et al. SHP-1 and SHP-2 associate with immunoreceptor tyrosine-based switch motif of programmed death 1 upon primary human T cell stimulation, but only receptor ligation prevents activation. *J. Immunol.* (2004): 173: 945-954.
5. Nishimura, H., Nose, M., Hiai, H. et al. Development of lupus-like autoimmune diseases by disruption of the PD-1 gene encoding an ITIM motif-carrying immunoreceptor. *Immunity* (1999); 11:141-151.
6. Okazaki T et al. Autoantibodies against cardiac troponin I are responsible for dilated cardiomyopathy in PD-1 deficient mice. *Nature Medicine* (2003): 9: 1477-1483.

7. Ansari M J. The programmed death-1 pathway regulates diabetes in nonobese diabetic (NOD) mice. *J Exp. Med.* (2003), July 7; 198(1):63-9.
8. Riley J and June C. The road to recovery: translating PD-1 biology into clinical benefit. *Trends in Immunology* (2006): 28:48-50.
9. Barber D L. Restoring function in exhausted CD8 T cells during chronic viral infection. *Nature* (2006):439: 682-687.
10. Trautmann L et al. Upregulation of PD-1 expression on HIV-specific CD8+ T cells leads to reversible immune dysfunction. *Nature Medicine* (2006) 12: 1198-1202.
11. Petrovas C et al. PD-1 is a regulator of virus-specific CD8+ T cell survival in HIV infection. *J Exp. Med.* (2006): 203: 2281-2292.
12. Day C L et al. PD-1 expression on HIV-specific T cells is associated with T-cell exhaustion and disease progression, Nature. 2006 Sep. 21; 443(7109):350-4.
13. Velu V et al. 2009. Enhancing SIV-specific immunity in vivo by PD-1 blockade. *Nature* (2009) 458: 206-210.
14. Finnefrock et al. PD-1 blockade in rhesus macaques: inpact on chronic infection and prophylactic vaccination. *J. of Immunol.* (2009): 182: 980-987.
15. Dong H et al. Tumor-associated B7-H1 promotes T-cell apoptosis: a potential mechanism of immune evasion. *Nat Med.* 2002 August; 8(8):793-800.
16. Yang et al. PD-1 interaction contributes to the functional suppression of T-cell responses to human uveal melanoma cells in vitro. *Invest Ophthalmol Vis Sci.* 2008 June; 49(6 (2008): 49: 2518-2525.
17. Ghebeh et al. The B7-H1 (PD-L1) T lymphocyte-inhibitory molecule is expressed in breast cancer patients with infiltrating ductal carcinoma: correlation with important high-risk propgnostic factors. *Neoplasia* (2006) 8: 190-198.
18. Hamanishi J et al. Programmed cell death 1 ligand 1 and tumor-infiltrating CD8+ T lymphocytes are prognostic factors of human ovarian cancer. *Proceeding of the National Academy of Sciences* (2007): 104: 3360-3365.
19. Thompson R H et al. Significance of B7-H1 overexpression in kidney cancer. Clinical genitourin *Cancer* (2006): 8: 206-211.
20. Nomi, T. Sho, M., Akahori, T., et al. Clinical significance and therapeutic potential of the programmed death-1 ligand/programmed death-1 pathway in human pancreatic cancer. *Clinical Cancer Research* (2007); 13:2151-2157.
21. Ohigashi Y et al. Clinical significance of programmed death-1 ligand-1 and programmed death-1 ligand 2 expression in human esophageal cancer. *Clin. Cancer Research* (2005): 11: 2947-2953.
22. Inman et al. PD-L1 (B7-H1) expression by urothelial carcinoma of the bladder and BCG-induced granulomata: associations with localized stage progression. *Cancer* (2007): 109: 1499-1505.
23. Shimauchi T et al. Augmented expression of programmed death-1 in both neoplasmatic and normeoplastic CD4+ T-cells in adult T-cell Leukemia/Lymphoma. *Int. J. Cancer* (2007): 121:2585-2590.
24. Gao et al. Overexpression of PD-L1 significantly associates with tumor aggressiveness and postoperative recurrence in human hepatocellular carcinoma. *Clinical Cancer Research* (2009) 15: 971-979.
25. Nakanishi J. Overexpression of B7-H1 (PD-L1) significantly associates with tumor grade and postoperative prognosis in human urothelial cancers. *Cancer Immunol Immunother.* (2007) 56: 1173-1182.
26. Hino et al. Tumor cell expression of programmed cell death-1 is a prognostic factor for malignant melanoma. *Cancer* (2010): 00:1-9.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. §1.57(b)(1), to relate to each and every individual publication, database entry (e.g. Genbank sequences or GeneID entries), patent application, or patent, each of which is clearly identified in compliance with 37 C.F.R. §1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

What is claimed is:

1. A stable lyophilized pharmaceutical formulation of an anti-human PD-1 antibody, wherein the formulation made by lyophilizing an aqueous solution comprising:
   a) 25-100 mg/mL of the anti-human PD-1 antibody;
   b) about 70 mg/mL sucrose;
   c) about 0.2 mg/mL polysorbate 80; and
   d) about 10 mM Histidine buffer at about pH 5.0-pH 6.0, and
   wherein the antibody, comprises:
      i) a light chain comprising amino acid residues 20 to 237 of SEQ ID NO: 36; and
      ii) a heavy chain comprising amino acid residues 20 to 466 of SEQ ID NO: 31.

2. The stable lyophilized pharmaceutical formulation of claim 1, wherein the anti-human PD-1 antibody is present at about 25 mg/mL in the aqueous solution.

3. The stable lyophilized pharmaceutical formulation of claim 1, wherein the aqueous solution has a pH of about 5.5.

4. The stable lyophilized pharmaceutical formulation of claim 1, wherein the aqueous solution comprises 25.0 mg/ml of the anti-human PD-1 antibody, 1.55 mg/ml histidine, 0.2 mg/ml polysorbate 80, 70 mg/ml sucrose, and has a pH of 5.5.

5. A stable liquid pharmaceutical formulation of an anti-human PD-1 antibody, comprising:
   a) 25-100 mg/mL of the anti-human PD-1 antibody;
   b) about 70 mg/mL sucrose;
   c) about 0.2 mg/mL polysorbate 80; and
   d) about 10 mM histidine buffer at pH 5.0-6.0,
   wherein the antibody comprises:
      i) a light chain comprising amino acid residues 20 to 237 of SEQ ID NO: 36; and
      ii) a heavy chain comprising amino acid residues 20 to 466 of SEQ ID NO:31, and
      wherein the liquid formulation has not been previously lyophilized.

6. The stable liquid pharmaceutical formulation of claim 5, which comprises 10 mM histidine, pH 5.5, 7% sucrose, 0.02% polysorbate 80, and 25.0 mg/ml of the anti-human PD-1 antibody.

7. A method of treating cancer in a human subject in need thereof, the method comprising administering an effective amount of a pharmaceutical formulation of an anti-human PD-1 antibody comprising:
   a) 25-100 mg/mL of the anti-human PD-1 antibody, or antigen binding fragment thereof;
   b) about 70 mg/mL sucrose;
   c) about 0.2 mg/mL polysorbate 80; and
   d) about 10 mM histidine buffer at pH 5.0-6.0,
   wherein the antibody comprises:
      i) a light chain comprising amino acid residues 20 to 237 of SEQ ID NO: 36; and
      ii) a heavy chain comprising amino acid residues 20 to 466 of SEQ ID NO:31, and
      wherein the pharmaceutical formulation is reconstituted from a stable lyophilized formulation or is a stable liquid formulation has not been previously lyophilized.

8. The method of claim 7, wherein the effective amount comprises a dose selected from the group consisting of about 1.0, 3.0, and 10 mg/kg administered at intervals of about 14 days or about 21 days throughout the course of treatment.

9. The method of claim 7, wherein the effective amount comprises a dose of 5.0 mg/kg or 10 mg/kg administered at intervals of every 2 weeks or every 3 weeks throughout the course of treatment.

10. The method of claim 7, wherein the subject has melanoma and the effective amount comprises a dose of 3.0 mg/kg administered at intervals of every 3 weeks throughout the course of treatment.

11. The method of claim 7, wherein the subject is treatment naïve.

12. The method of claim 7, wherein the pharmaceutical formulation is administered in a 30 minute IV infusion.

13. The method of claim 7, wherein the subject has melanoma.

* * * * *